US009624436B2

(12) United States Patent
Hamilton et al.

(10) Patent No.: US 9,624,436 B2
(45) Date of Patent: *Apr. 18, 2017

(54) METHODS AND SYSTEMS FOR PROCESSING BIOMASS MATERIAL

(71) Applicant: SHELL OIL COMPANY, Houston, TX (US)

(72) Inventors: Phillip Guy Hamilton, Sugar Land, TX (US); Corey William Radtke, Katy, TX (US); Keith Michael Kreitman, Houston, TX (US); Paul Richard Weider, Houston, TX (US); Robert Lawrence Blackbourn, Houston, TX (US)

(73) Assignee: SHELL OIL COMPANY, Houston, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 13/895,931

(22) Filed: May 16, 2013

(65) Prior Publication Data
US 2013/0309727 A1 Nov. 21, 2013

Related U.S. Application Data

(60) Provisional application No. 61/648,109, filed on May 17, 2012, provisional application No. 61/786,860, filed on Mar. 15, 2013, provisional application No. 61/786,844, filed on Mar. 15, 2013.

(51) Int. Cl.
| | |
|---|---|
| C12P 7/00 | (2006.01) |
| C10G 1/00 | (2006.01) |
| C12P 7/06 | (2006.01) |
| C12P 5/00 | (2006.01) |
| C12F 3/10 | (2006.01) |
| C10G 3/00 | (2006.01) |
| C12P 7/10 | (2006.01) |
| C12P 5/02 | (2006.01) |
| C10G 1/02 | (2006.01) |

(52) U.S. Cl.
CPC .............. *C10G 1/002* (2013.01); *C10G 1/02* (2013.01); *C10G 3/46* (2013.01); *C10G 3/50* (2013.01); *C12F 3/10* (2013.01); *C12P 5/00* (2013.01); *C12P 5/02* (2013.01); *C12P 5/026* (2013.01); *C12P 7/00* (2013.01); *C12P 7/06* (2013.01); *C12P 7/10* (2013.01); *Y02E 50/16* (2013.01); *Y02E 50/17* (2013.01); *Y02E 50/343* (2013.01); *Y02P 30/20* (2015.11); *Y02T 50/678* (2013.01)

(58) Field of Classification Search
None
See application file for complete search history.

(56) References Cited

U.S. PATENT DOCUMENTS

| | | |
|---|---|---|
| 3,549,319 A | 12/1970 | Wilson |
| 4,503,079 A | 3/1985 | King et al. |
| 5,536,325 A | 7/1996 | Brink |
| 5,789,210 A | 8/1998 | Ho et al. |
| 6,475,768 B1 | 11/2002 | Otero et al. |
| 6,673,596 B1 | 1/2004 | Sayler et al. |
| 6,818,803 B1 | 11/2004 | Austin-Phillips et al. |
| 7,285,179 B2 | 10/2007 | Snekkenes et al. |
| 7,510,857 B2 | 3/2009 | Brumm |
| 7,781,191 B2 | 8/2010 | Dunson, Jr. et al. |
| 7,973,199 B2 | 7/2011 | Masuda et al. |
| 8,641,910 B2 | 2/2014 | Wietgrefe |
| 8,658,407 B2 | 2/2014 | Lyons et al. |
| 8,835,156 B2 | 9/2014 | Bjornsson et al. |
| 2003/0162271 A1 | 8/2003 | Zhang et al. |
| 2006/0292264 A1 | 12/2006 | Young et al. |
| 2008/0216391 A1 | 9/2008 | Cortright et al. |

(Continued)

FOREIGN PATENT DOCUMENTS

| | | |
|---|---|---|
| CN | 1140556 | 1/1997 |
| CN | 101085995 | 6/2007 |

(Continued)

OTHER PUBLICATIONS

Shen, Fei; Liu, Ronghou; "Research on Solid-State Ethanol Fermentation Using Dry Sweet Sorghum Stalk Particles with Active Dry Yeast" Energy & Fuels, 23, 519-525, 2009.*
Bahrin, Ezyana Kamal; et al; "Physicochemical Property Changes and Enzymatic Hydrolysis Enhancement of Oil Palm Empty Fruit Bunches Treated with Superheated Steam" Bioresources, 7, 1784-1801, 2012.*
Zhao, Xuebing; et al; "Organosolv pretreatment of lignocellulosic biomass for enzymatic hydrolysis" Applied Microbiology and Biotechnology, 82, 815-827, 2009.*
Kumar, Parveen; et al; "Methods for Pretreatment of Lignocellulosic Biomass for Efficient Hydrolysis and Biofuel Production" Industrial & Engineering Chemistry Research, 48, 3713-3729, 2009.*
Pushalkar, S; Rao, KK; "Short Communication: Ethanol fermentation by a cellulolytic fungus Aspergillus terreus" World Journal of Microbiology & Biotechnology, 14, 289-291, 1998.*
Zhu and Pan; Bioresource Technology; vol. 100; pp. 10-18; 2010.
Hendriks and Zeeman; Bioresource Technology; vol. 100; pp. 10-18.
Renon, et al: "Local Compositions in Thermodynamic Excess Functions for Liquid Mixtures"; AIChE Journal; vol. 14, No. 1: pp. 135-144; Jan. 1998.

(Continued)

Primary Examiner — Renee Claytor
Assistant Examiner — David Berke-Schlessel

(57) ABSTRACT

Embodiments of the present invention provide for efficient and economical production and recovery of ethanol or other volatile organic compounds. One embodiment comprises contacting a solid component of a biomass material with a solution adapted to facilitate saccharification. The solid component is generated by a method comprising: introducing a biomass material to a compartment of a solventless recovery system, wherein the biomass material contains one or more volatile organic compounds; contacting the biomass material with a superheated vapor stream in the compartment to vaporize at least a portion of an initial liquid content in the biomass material; separating a vapor component and a solid component from the heated biomass material; and retaining at least a portion of the gas component for use as part of the superheated vapor stream. In one embodiment, the solid component contacted with the solution is further subjected to enzymatic hydrolysis and/or fermentation.

29 Claims, 8 Drawing Sheets

(56) References Cited

U.S. PATENT DOCUMENTS

| | | | |
|---|---|---|---|
| 2009/0226571 | A1 | 9/2009 | Freyer et al. |
| 2009/0239279 | A1 | 9/2009 | Hall et al. |
| 2010/0236988 | A1 | 9/2010 | Gabrielov et al. |
| 2010/0248320 | A1 | 9/2010 | Lyons et al. |
| 2010/0249470 | A1 | 9/2010 | Schirmer et al. |
| 2011/0015445 | A1 | 1/2011 | Masuda et al. |
| 2011/0100359 | A1 | 5/2011 | North |
| 2011/0108409 | A1* | 5/2011 | Brown .............................. 203/42 |
| 2011/0154721 | A1 | 6/2011 | Chheda et al. |
| 2011/0154722 | A1 | 6/2011 | Chheda et al. |
| 2011/0282115 | A1 | 11/2011 | Chheda et al. |
| 2012/0317872 | A1 | 12/2012 | Powell et al. |
| 2013/0052709 | A1 | 2/2013 | Wietgrefe et al. |
| 2013/0173562 | A1 | 7/2013 | Allspector et al. |
| 2013/0305598 | A1 | 11/2013 | Hamilton et al. |

FOREIGN PATENT DOCUMENTS

| | | |
|---|---|---|
| CN | 101300359 | 11/2008 |
| CN | 101503713 | 8/2009 |
| CN | 101235391 | 8/2011 |
| CN | 101268121 | 11/2011 |
| CN | 102399826 | 4/2012 |
| CN | 102449156 | 5/2012 |
| GB | 2141316 | 9/1988 |
| GB | 2201413 | 9/1988 |
| JP | 2009136201 | 6/2009 |
| JP | 2009136202 | 6/2009 |
| JP | 2009209059 | 9/2009 |
| JP | 2009535038 | 10/2009 |
| JP | 2011182685 | 9/2011 |
| JP | 2012055302 | 3/2012 |
| WO | 9113099 | 9/1991 |
| WO | 9513362 | 5/1995 |
| WO | 9742307 | 11/1997 |
| WO | 9745430 | 12/1997 |
| WO | 9811235 | 3/1998 |
| WO | 2005093041 | 10/2005 |
| WO | 2006096130 | 9/2006 |
| WO | 2007028811 | 3/2007 |
| WO | 2007100897 | 9/2007 |
| WO | 2007127912 | 11/2007 |
| WO | 2007136762 | 11/2007 |
| WO | 2008119082 | 10/2008 |
| WO | 2009058276 | 5/2009 |
| WO | 2009109631 | 9/2009 |
| WO | WO2010028206 | 3/2010 |
| WO | 2010065643 | 6/2010 |
| WO | 2010096510 | 8/2010 |
| WO | WO2010096510 | 8/2010 |
| WO | 2010107944 | 9/2010 |
| WO | 201139635 | 4/2011 |
| WO | 2011039635 | 4/2011 |
| WO | 2011057159 | 5/2011 |
| WO | 2011082000 | 7/2011 |
| WO | WO2011149956 | 12/2011 |
| WO | 2011143391 | 5/2012 |
| WO | 2012061596 | 5/2012 |
| WO | WO2012061596 | 5/2012 |
| WO | 2013173560 | 11/2013 |
| WO | 2013173562 | 11/2013 |

OTHER PUBLICATIONS

Henk, L. et al.; "Solid State Production of Ethanol from Sorghum"; Applied Biochemistry and Biotechnology; vol. 57/58; pp. 489-501; 1996.

Webster, W, et al: "Observations of the Harvesting, Transporting and Trial Crushing of Sweet Sorghum in a Sugar Mill"; 2004 Conference of the Australian Society of Sugar Cane Technologist; Queensland, Australia; 2 pages;; May 2004.

Andrzejewski et al.; "Development of commercially viable processing technologies for sweet sorghum"; USDA-ARS-Southern Regional Research Center; Sweet Sorghum Ethanol Conference; Jan. 26, 2012.

Bellmer, D; "The untapped potential of Sweet Sorghum as a Bioenergy Feedstock"; Sweet Sorghum ethanol Conference; pp. 1-33; Jan. 26, 2012.

Wu et al.; "Features of sweet sorghum juice and their performance in ethanol fermentation"; Industrial Crops and Products; vol. 31; pp. 164-170; 2010.

Bennet et al; "Farm-gate productions costs of sweet sorghum as a bioethanol feedstock"; Transactions of the American Society of Agricultural and Biological Engineers; vol. 5(2); pp. 602-613; 2008.

Shen et al.; "Research on Solid-State Ethanol Fermentation Using Dry Sweet Sorghum Stalk Particles with Active Dry Yeast"; Energy & FUels; vol. 23; pp. 519-525; 2009.

Iman et al.; Ethanol Fermentation from Sweet Sorghum Juice; ASABE Annual International Meeting; Pittsburge, PA; pp. 1-8; Jun. 2010.

Lingle, et al.; "Post-harvest Changes in Sweet Sorghum I: Brix and Sugars"; Bioenerg. Res.; vol. 5; pp. 158-167; 2012.

Radtke, et al. "Milestone Completion Report"; Idaho National Laboratory; pp. 1-30; Sep. 29, 2007.

Noah, et al.; "Extraction of Ensiled Sweet Sorghum with a Continuous Countercurrent Diffuser"; American Society of Agricultural Engineers; vol. 32, No. 4; pp. 1419-1425; Jul.-Aug. 1989.

Schmidt, et al.; "Preservation of Sugar Content in Ensiled Sweet Sorghum"; Bioresource Technology; vol. 60; pp. 9-13; 1997.

Bellmer, et al. "The untapped potential of sweet sorghum as a bioenergy feedstock"; Biofuels, vol. 1(4); pp. 563-573; 2010.

Radtke, et al., Crossover 2007 Bioenergy: From Fields to Wheels Presentation; pp. 1-22; Sep. 4, 2007.

Brooks et al.; "Bioconversion of plant biomass to ethanol"; Sol. Energy Res. Inst.; Biomass Energy Syst. Conf. Proc.; 3rd; pp. 275-280; 1979.

Morgan et al; Volatile constituents of grass and corn silage.I. Steam distillates; Journal of Dairy Science; vol. 45, No. 4; pp. 457-466; Apr. 22, 2001.

Database WPI; Week 200873; Thomson Scientific; London; GB; AN 2008-M35687; XP002711690.

International Search Report for PCT/US2013/041309 dated Sep. 5, 2013; 5 pages.

International Search Report for PCT/US2013/041313 dated Sep. 2, 2013; 5 pages.

Li, et al.; "Renewable Gasoline from Aqueous Phase Hydrodeoxygenation of Aqueous Sugar Solutions prepared by Hydrolysis of Maple Wood"; The Royal Society of Chemistry; Green Chemistry; vol. 13; No. 1; pp. 91-101; Jan. 2011.

Kitamoto, et al.; "Production of bio-ethanol by solid state fermentation of cellulosic biomass"; National Institute for Agro-Environmental Sciences; vol. 26, No. 12; pp. 52-57; 2009.

Brooks, et al.; "Bioconversion of plant biomass to ethanol"; Sol. Energy Res. Inst.; Biomass Energy Syst. Conf. Proc.; 3rd; pp. 275-280; 1979.

Database WPI, Week 200873; Thomson Scientific; London; GB, AN 2008-M35687; XP002711690 = to Chinese Patent No. 101235391.

International Search Report for PCT/US2013/041327 dated May 16, 2013; 5 pages.

Bahree, M., "Sorghum for Ethanol", International United Phosphorous Fuel Sorghum, Forbes Magazine, 2009, pp. 1-6.

Brooks, et al., "Bioconversion of Plant Biomass to Ethanol", Sol. Energy Res. Inst., Biomass Energy Syst. Conf. Proc.,1979, 3rd Ed., pp. 275-280.

www.azda.gov, "Agriculture Improving Air Quality", Guide to Agriculture PM10 Best Management Practices, Governor's Agriculture BMP Committee, 2008, pp. 1-29.

GEA Barr-Rosin, "Superheated Steam Dryer and Processor", Environmental and Energy Saving Drying Technology Treatment of Oil Seeds, Beans and Proteins, Brochure, GEA Group AG.

Gupta, R. et al., "Liquid-Liquid Extraction Using the Composition-Induced Phase Separation Process", Ind. Eng. Chem. Res., 1996, vol. 35, pp. 2360-2368.

Morey, R.V. et al., "Superheated Steam Drying Technology in an Ethanol Production Process", An ASABE Meeting Presentation, Paper No. 1009069, 2010, Pittsburgh, PA, pp. 1-11.

(56) References Cited

OTHER PUBLICATIONS

Needleman, S. B. et al., A General Method Applicable to the Search for Similarities in the Amino Acid Sequence of Two Proteins, 1970, J. Mol. Biol., vol. 48, pp. 443-453.

Zhu, J.Y. et al., "Woody Biomass Pretreatment for Cellulosic Ethanol Production, Technology and Energy Consumption Evaluation", Bioresource Technology, vol. 101, 2010, pp. 4992-5002.

Bryan, W. L., "Solid-State Fermentation of Sugars in Sweet Sorghum", Enzyme Microb. Technol., 1990, vol. 12, pp. 437-442.

Gan, Z. et al., "Effects of the DDGS (Corn) Selection and Production Process on Quality", Feed & Animal Husbandry, 2009, No. 11, pp. 15-20.

Kosaric N. et al., "Ethanol", Ullmanns Encyclopedia of Industrial Chemistry, 2011, vol. 13, pp. 333-403.

Sagehashi M. et al., "Superheated Steam Pyrolysis of Biomass Elemental Components and Sugi (Japanese cedar) for Fuels and Chemicals," Bioresource Technology, Elsevier BV, GB, vol. 97, No. 11, 2006, pp. 1272-1283.

Sousa S. et al., "The AR04 Gene of Candida Albicans Encodes a Tyrosine-Sensitive DAHP Synthase: Evolution, Functional Conservation and Phenotype of ARO3p-, ARO4p-Deficient Mutants", Microbiology, 2002, vol. 148, 1291-1303.

Tian, Z., "Non-Polluting Feed Formulation Technologies for Domestic Livestock", (National Pollution-Free Food Action Plant Series) Beijing, China Agriculture Press, 2011, 2nd Ed., p. 89.

PCT International Searching Authority, Search Report mailed Aug. 19, 2013, Application No. PCT/US2013/041306 filed May 16, 2013.

PCT International Searching Authority, Search Report mailed Oct. 23, 2013, Application No. PCT/US2013/041339 filed May 16, 2013.

\* cited by examiner

METHODS AND SYSTEMS FOR PROCESSING BIOMASS MATERIAL

CROSS-REFERENCE TO RELATED APPLICATIONS

This application claims the benefit of U.S. Application No. 61/648,109 filed on May 17, 2012 and U.S. Application No. 61/786,844 filed Mar. 15, 2013, and U.S. Provisional Application No. 61/786,860, filed on Mar. 15, 2013, the disclosures of which are incorporated by reference herein in their entirety.

FIELD OF THE INVENTION

Embodiments of this invention relate generally to a process for the manufacture of volatile organic compounds from biomass material and more particularly to manufacturing and recovery of volatile organic compounds using fermentation of readily available fermentable sugar and production of fermentable sugar from further processing of lignocellulosic material in the biomass material.

BACKGROUND

This section is intended to introduce various aspects of the art, which may be associated with exemplary embodiments of the present invention. This discussion is believed to assist in providing a framework to facilitate a better understanding of particular aspects of the present invention. Accordingly, it should be understood that this section should be read in this light, and not necessarily as admissions of any prior art.

As the world's petroleum supplies continue to diminish there is a growing need for alternative materials that can be substituted for various petroleum products, particularly transportation fuels. A significant amount of effort has been placed on developing new methods and systems for providing energy from resources other than fossil fuels. Currently, much effort is underway to produce bioethanol and other transportation fuels and chemicals from renewable biomass materials. One type of biomass is plant biomass, which contains a high amount of carbohydrates including sugars, starches, celluloses, lignocelluloses, hemicelluloses. Efforts have particularly been focused on ethanol from fermentable sugar readily available and ethanol from cellulosic materials.

Conventional ethanol production from corn typically competes with valuable food resources, which can be further amplified by increasingly more severe climate conditions, such as droughts and floods, which negatively impact the amount of crop harvested every year. The competition from conventional ethanol production can drive up food prices. While other crops have served as the biomass material for ethanol production, they usually are not suitable for global implementations due to the climate requirements of such crops. For instance, ethanol can also be efficiently produced from sugar cane, but only in certain areas of the world, such as Brazil, that have a climate that can support near-year-round harvest.

Further, additional fermentable sugars can be freed from lignocellulosic biomass, which comprises hemicelluloses, cellulose and smaller portions of lignin and protein. Cellulose comprises sugars that can be converted into fuels and valuable chemicals, when they are liberated from the cell walls and polymers that contain them.

Current processes aiming to process lignocellulosic biomass are limited to feedstock that includes unprocessed biomass materials or municipal solid waste (MSW). Unprocessed biomass includes sugarcane bagasse, forest resources, crop residue, and wet/dry harvested energy crops. These conventional feedstock sources require storage, transportation, particle size reduction, and additional front end processing before they can be introduced for further processing of lignocellulosic material. For example, baling of biomass is costly and can result in hazards such as fire, rodent, dust, unwanted debris (such as rocks) and hantavirus. Further, bales and forest resources are more costly to transport than denser material and more costly to handle than materials that are already particle size reduced and do not need to be further formatted. MSW further has challenges related to contamination with regulated hazardous metals that can contribute to risks of poor fuel quality as well as health and safety risks. Forest resources, such as trees, are cumbersome to transport. Further, forest resources require debarking, chopping to wood chips of desirable thickness, and washing to remove any residual soil, dirt and the like. Therefore, there is still a need for a biomass that addresses these challenges.

SUMMARY

Embodiments of the invention can address the challenges mentioned above as well as provide other advantages and features. In one embodiment, the feedstock can come from the solid component exiting a volatile organic compound recovery system. In that embodiment, the feedstock is already flowable in an engineered system, which allows the feedstock to be routed directly into the reactor to generate additional fermentable sugars as desired. Embodiments of the invention can provide for a volatile organic compound recovery equipment to recover products from the fermentation phase and further processing of lignocellulosic material equipment to be located near each other. The further processing can yield additional fermentable sugar that can be converted to various volatile organic compounds. Such embodiments can allow for production of volatile organic compounds from fermentation and further processing of lignocellulosic material, which reduces storage, handling, and transportation costs associated with other feedstock before it can enter the production flow of the further processing of lignocellulosic material. Such embodiments can also provide a continuous supply of feedstock that is already formatted in contrast to conventional feedstock that often requires storage, transportation, and/or formatting at or prior to arriving at the biomass plant for processing of the lignocellulosic material, which reduces particular associated costs.

The feedstock of certain embodiments can also have lower handling and transportation costs when it is transported to other locations for processing of the lignocellulosic material. Unlike other conventional feedstock sources, such as forest resources, the feedstock of certain embodiments exits the volatile organic compound recovery system in a preformatted manner that is particle-size reduced, which can reduce or eliminate the front end processing costs before the feedstock can enter the processing of lignocellulosic material. The preformatted size distribution of the feedstock of certain embodiments of the invention places it in a denser form than other conventional feedstock sources, which can reduce transportation cost as more of the feedstock of these embodiments can be transported per volume. Embodiments of the invention can provide a supply of feedstock that is available year-round independent of a harvest period particular to a biomass material thus reducing storage needs and costs for the further processing plant and does not compete with valuable food sources for human.

Moreover, in certain embodiments, the solid component obtained according to aspects of the invention can allow for better saccharification, particularly pretreatment and enzymatic hydrolysis, as compared to other biomass feedstock sources, such as corn stover. In a particular embodiment, the solid component can achieve the same or better glucose production after pretreatment with alpha-hydroxyethane sulfonic acid (HESA) and enzymatic hydrolysis without agitation or mixing (such as stirring) of the pretreatment reaction mixture. Minimizing or eliminating such mixing or agitation requirement at least during pretreatment can allow for a simpler and more economical scale up (such as commercial scale) operations. In certain embodiments that may not require mixing to achieve pretreatment targets, less consideration is needed during scaling up for parameters such as power per unit volume, pumping capacity of the impeller per unit volume, sheer stress curves, reactor geometry and ultimately Reynolds number, particularly for heterogeneous, fibrous systems such as biomass/water systems. As such, certain embodiments of the invention can allow for less expensive equipment, and the associated maintenance, that may be required for mixing.

In one embodiment, a biomass material is prepared to generate volatile organic compounds. The volatile organic compounds are recovered from the prepared biomass material by introducing the prepared biomass material to a compartment of a solventless recovery system; contacting the biomass material with a superheated vapor stream in the compartment to vaporize at least a portion of an initial liquid content in the prepared biomass material, the superheated vapor stream comprising at least one volatile organic compound; separating a vapor component and a solid component from the heated biomass material, where the vapor component comprises at least one volatile organic compound; and retaining at least a portion of the gas component for use as part of the superheated vapor stream. Compounds in the vapor component can be further purified through an appropriate distillation process. At least a portion of the solid component is further processed to generate additional fermentable sugars. In one embodiment, the further processing comprises contacting at least a portion of the solid component with a solution adapted to facilitate saccharification. In one embodiment, the additionally generated fermentable sugars are fermented to produce a plurality of volatile organic compounds, such as ethanol. In a particular embodiment, liquid from the fermented mixture may be routed to the distillation process of the vapor component, thereby allowing for an integrated system to generate ethanol from a majority of the carbohydrates contained in a biomass material (such as readily available fermentable sugars and those generated from further processing of lignocellulosic material).

In one embodiment, the prepared biomass is generated by adding to the biomass at least one additive added, wherein said at least one additive comprise a microbe, and optionally, an acid and/or an enzyme; and storing the prepared biomass material for at least about 24 hours in a storage facility to allow for the production of at least one volatile organic compound from at least a portion of the sugar.

In addition to the features described above, embodiments of the invention allow for economical production of alternative fuels, such as ethanol, other volatile organic compounds, hydrocarbons, and other chemicals, from plants that contain fermentable sugar by addressing challenges, such as costs of storage and transportation, short harvest windows, quick degradation of sugars, and large investment in equipment. Aspects of the embodiments described herein are applicable to any biomass material, such as plants containing fermentable sugars. The features of embodiments of the present invention allow for economical use of various plants to produce alternative fuels and chemicals and are not limited to sorghum and other plants that suffer similar challenges. Such challenging crops are highlighted herein because other methods and systems have not been able to economically use these challenging crops to produce fuels and chemicals. As such, the specific mention of sorghum is not intended to be limiting, but rather illustrates one particular application of embodiments of the invention.

Embodiments of the invention allow for the recovery facility to run continuously year-round in a controlled manner independent of the harvest window, thereby broadening the geological locations available to place a recovery facility and/or a facility to process lignocellulosic material, including areas with a relatively short harvest window.

Other advantages and features of embodiments of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWING

These drawings illustrate certain aspects of some of the embodiments of the invention, and should not be used to limit or define the invention.

DETAILED DESCRIPTION OF PREFERRED EMBODIMENTS

Figure 1:
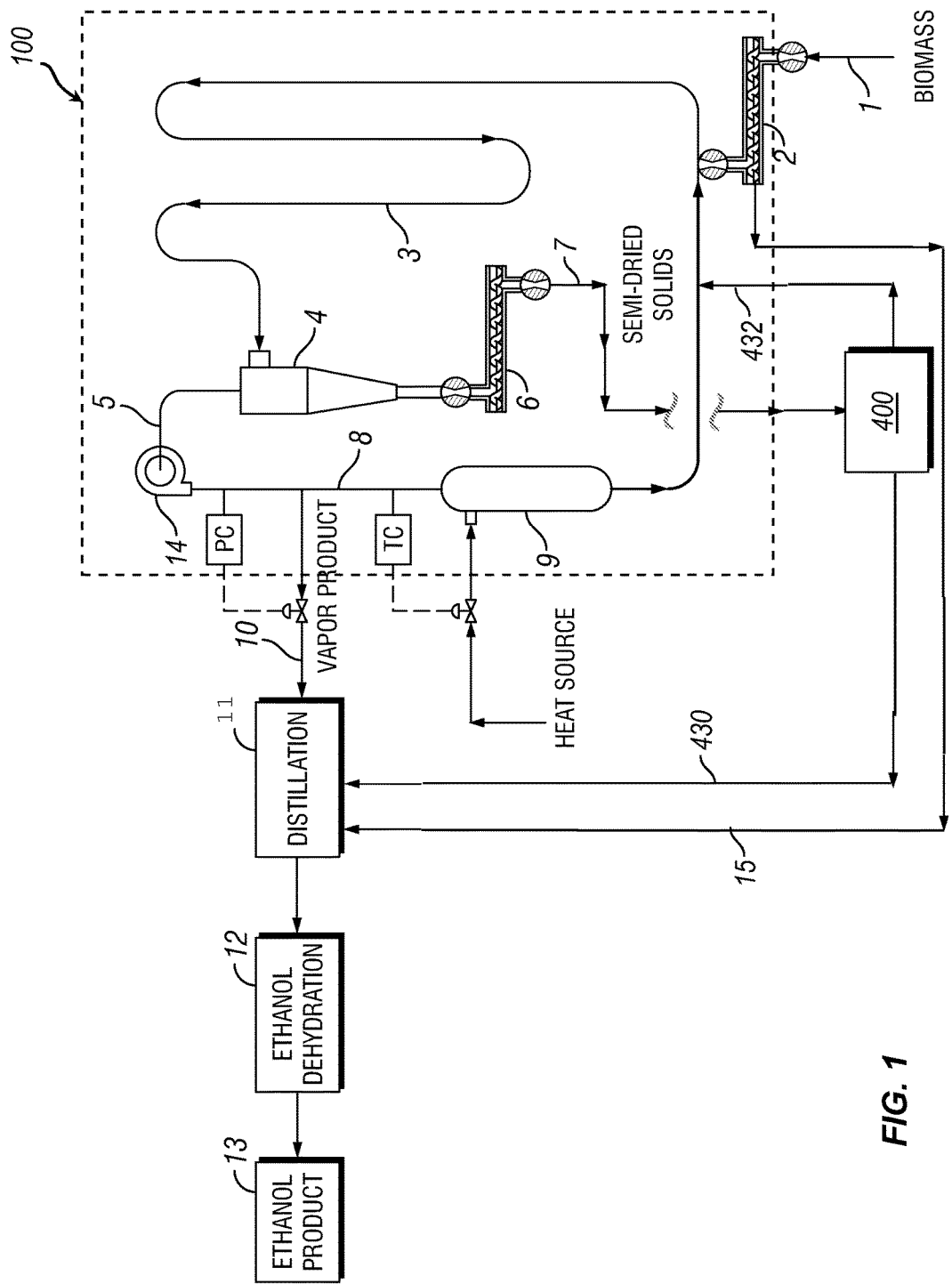
FIG. 1 is a diagram of one embodiment to process biomass material according to certain aspects of the present invention.

Embodiments of the present invention can provide efficient and economical production and recovery of ethanol or other volatile organic compounds, such as acetic acid, from solid biomass material, as well as a feedstock for further processing of lignocellulosic material to generate fermentable sugar. According to one aspect of the invention, a biomass material is prepared to generate volatile organic compounds. The volatile organic compounds are recovered from the prepared biomass material by introducing the prepared biomass material to a compartment of a solventless recovery system; contacting the biomass material with a superheated vapor stream in the compartment to vaporize at least a portion of an initial liquid content in the prepared biomass material, the superheated vapor stream comprising at least one volatile organic compound; separating a vapor component and a solid component from the heated biomass material, where the vapor component comprises at least one volatile organic compound; and retaining at least a portion of the gas component for use as part of the superheated vapor stream. At least a portion of the solid component is further processed to generate additional fermentable sugar. In one embodiment, the further processing contacting at least a portion of the solid component with a solution adapted to facilitate saccharification. In one embodiment, the additionally generated fermentable sugars are fermented to produce a plurality of volatile organic compounds, such as ethanol.

Biomass Preparation

As used herein, the term "solid biomass" or "biomass" refers at least to biological matter from living, or recently living organisms. Solid biomass includes plant or animal matter that can be converted into fibers or other industrial chemicals, including biofuels. Solid biomass can be derived from numerous types of plants or trees, including miscanthus, switchgrass, hemp, corn, tropical poplar, willow, sorghum, sugarcane, sugar beet, and any energy cane, and a variety of tree species, ranging from eucalyptus to oil palm (palm oil). In one embodiment, the solid biomass comprises at least one fermentable sugar-producing plant. The solid biomass can comprise two or more different plant types, including fermentable sugar-producing plant. In a preferred embodiment not intended to limit the scope of the invention, sorghum is selected, due to its high-yield on less productive lands and high sugar content.

The term "fermentable sugar" refers to oligosaccharides and monosaccharides that can be used as a carbon source (e.g., pentoses and hexoses) by a microorganism to produce an organic product such as alcohols, organic acids, esters, and aldehydes, under anaerobic and/or aerobic conditions. Such production of an organic product can be referred to generally as fermentation. The at least one fermentable sugar-producing plant contains fermentable sugars dissolved in the water phase of the plant material at one point in time during its growth cycle. Non-limiting examples of fermentable sugar-producing plants include sorghum, sugarcane, sugar beet, and energy cane. In particular, sugarcane, energy cane, and sorghum typically contain from about 5% to about 25% soluble sugar w/w in the water phase and have moisture content between about 60% and about 80% on a wet basis when they are near or at their maximum potential fermentable sugar production (e.g., maximum fermentable sugar concentration).

The term "wet basis" refers at least to the mass percentage that includes water as part of the mass. In a preferred embodiment, the sugar producing plant is sorghum. Any species or variety of the genus sorghum that provides for the microbial conversion of carbohydrates to volatile organic compounds (VOCs) can be used. For embodiments using sorghum, the plant provides certain benefits, including being water-efficient, as well as drought and heat-tolerant. These properties make the crop suitable for many locations, including various regions across the earth, such as China, Africa, Australia, and in the US, such as portions of the High Plains, the West, and across the South. Tex.

In embodiments using sorghum, the sorghum can include any variety or combination of varieties that may be harvested with higher concentrations of fermentable sugar. Certain varieties of sorghum with preferred properties are sometimes referred to as "sweet sorghum." The sorghum can include a variety that may or may not contain enough moisture to support the juicing process in a sugar cane mill operation. In a preferred embodiment, the solid biomass includes a Sugar T sorghum variety commercially produced by Advanta and/or a male parent of Sugar T, which is also a commercially available product of Advanta. In a preferred embodiment, the crop used has from about 5 to about 25 brix, preferably from about 10 to about 20 brix, and more preferably from about 12 to about 18 brix. The term "brix" herein refers at least to the content of glucose, fructose, and sucrose in an aqueous solution where one degree brix is 1 gram of glucose, fructose, and/or sucrose in 100 grams of solution and represents the strength of the solution as percentage by weight (% w/w). In another preferred embodiment, the moisture content of the crop used is from about 50% to 80%, preferably at least 60%.

In one embodiment, the crop is a male parent of Sugar T with a brix value of about 18 and a moisture content of about 67%. In another embodiment, the crop is Sugar T with a brix value of about 12 at a moisture content of about 73%. In these particular embodiments, the brix and moisture content values were determined by handheld refractometer.

After at least one additive (a microbe, optionally, an acid and/or enzyme) is added to the solid biomass, it becomes prepared biomass material where the at least one additive facilitates the conversion of fermentable sugar into a VOC (such as ethanol). As noted above and further described below, the prepared biomass material can be stored for a certain period of time to allow more VOCs to be generated by the conversion process. At least one volatile organic compound is then recovered from the prepared biomass material. Volatile organic compounds are known to those skilled in the art. The U.S. EPA provides descriptions volatile organic compounds (VOC), one of which is any compound of carbon, excluding carbon monoxide, carbon dioxide, carbonic acid, metallic carbides or carbonates, and ammonium carbonate, which participates in atmospheric photochemical reactions, except those designated by EPA as having negligible photochemical reactivity. Another description of volatile organic compounds, or VOCs, is any organic chemical compound whose composition makes it possible for them to evaporate under normal indoor atmospheric conditions of temperature and pressure. This is the general definition of VOCs that is used in the scientific literature, and is consistent with the definition used for indoor air quality. Normal indoor atmospheric conditions of temperature and pressure refer to the range of conditions usually found in buildings occupied by people, and thus can vary depending on the type of building and its geographic location. One exemplary normal indoor atmospheric condition is provided by the International Union of Pure and Applied Chemistry (IUPAC) and the National Institute of Standards and Technology (NIST). IUPAC's standard is a temperature of C (273, 15 K, 32° F.) and an absolute pressure of 100 kPa (14.504 psi), and NIST's definition is a temperature of 20° C. (293, 15 K, 68° F.) and an absolute pressure of 101.325 kPa (14.696 psi).

Since the volatility of a compound is generally higher the lower its boiling point temperature, the volatility of organic compounds are sometimes defined and classified by their boiling points. Accordingly, a VOC can be described by its boiling point. A VOC is any organic compound having a boiling point range of about 50 degrees C. to 260 degrees C.

measured at a standard atmospheric pressure of about 101.3 kPa. Many volatile organic compounds that can be recovered and/or further processed from VOCs recovered from embodiments of the present invention have applications in the perfume and flavoring industries. Examples of such compounds may be esters, ketones, alcohols, aldehydes, hydrocarbons and terpenes. The following Table 1 further provides non-limiting examples of volatile organic compounds that may be recovered and/or further processed from VOCs recovered from the prepared biomass material.

TABLE 1

| | | | |
|---|---|---|---|
| Methanol | Ethyl acetate | Acetaldehyde | Diacetyl |
| 2,3-pentanedione | Malic acid | Pyruvic acid | Succinic acid |
| Butyric acid | Formic acid | Acetic acid | Propionic acid |
| Isobutyric acid | Valeric acid | Isovaleric acid | 2-methylbutyric acid |
| Hexanoic acid | Heptanoic acid | Octanoic acid | Nonanoic acid |
| Decanoic acid | Propanol | Isopropanol | Butanol |
| Isobutanol | Isoamyl alcohol | Hexanol | Tyrosol |
| Tryptoptanol | Phenethyl alcohol | 2,3-butanediol | Glycerol |
| Fumaric acid | Ethanol | Amyl alcohol | 1,2-propanol |
| 1-propanol | 2-butanol | Methyl acetate | Ethyl acetate |
| Propyl acetate | Ethyl lactate | Propyl lactate | Acetone |
| Ethyl formate | n-propyl alcohol | 2-methyl-1-propanol | 2-propen-1-ol |
| 2,3-methyl-1-butanol | 3-buten-2-ol | | |

Ethanol is a preferred volatile organic compound. As such, many examples specifically mention ethanol. This specific mention, however, is not intended to limit the invention. It should be understood that aspects of the invention also equally apply to other volatile organic compounds. Another preferred volatile organic compound is acetic acid.

Embodiments of the present invention provide for the long term storage of solid biomass material without significant degradation to the volatile organic compounds contained in the prepared biomass material, and they provide for sugar preservation to allow for continued generation of VOCs. As used in this context, "significant" refers at least to within the margin of error when measuring the amount or concentration of the volatile organic compounds in the prepared biomass material. In one embodiment, the margin of error is about 0.5%.

Accordingly, embodiments of the present invention allow for continuous production VOCs without dependence on the length of the harvest, thereby eliminating or minimizing down time of a recovery plant in traditional just-in-time harvest and recovery processes. As such, embodiments of the present invention allow for harvest of the crop at its peak without compromises typically made to lengthen the harvest season, such as harvest slightly earlier and later than peak time. That is, embodiments of the invention allow for harvest at high field yields and high sugar concentrations, such as when the selected crop has reached its peak sugar concentration or amount of fermentable sugars that can be converted into a volatile organic compound, even if this results in a shorter harvest period. In one embodiment, the solid biomass is harvested or prepared when it is at about 80%, about 85%, about 90%, about 95%, or about 100% of its maximum potential fermentable sugar concentration. As such, embodiments of the present invention, particularly the recovery phase, can be operated continuously year-round without time pressure from fear of spoilage of the solid biomass and VOCs contained therein. While embodiments of the present invention allow for harvest of the solid biomass near or at its maximum sugar production potential, the solid biomass material can be harvested at any point when it is deemed to contain a suitable amount of sugar.

Further, the harvest window varies depending on the type of crop and the geographical location. For example, the harvest window for sorghum in North America can range from about 1 to 7 months. However, in Brazil and other equatorial and near equatorial areas, the harvest window may be up to twelve months.

In embodiments using plants as the solid biomass, the solid biomass can be collected or harvested from the field using any suitable means known to those skilled in the art. In one embodiment, the solid biomass comprises a stalk component and a leaf component of the plant. In another embodiment, the solid biomass further comprises a grain component. In a preferred embodiment, the solid biomass is harvested with a forage or silage harvester (a forage or silage chopper). A silage or forage harvester refers to farm equipment used to make silage, which is grass, corn or other plant that has been chopped into small pieces, and compacted together in a storage silo, silage bunker, or in silage bags. A silage or forage harvester has a cutting mechanism, such as either a drum (cutterhead) or a flywheel with a number of knives fixed to it, which chops and transfers the chopped material into a receptacle that is either connected to the harvester or to another vehicle driving alongside. A forage harvester is preferred because it provides benefits over a sugar cane harvester or dry baled system. For example, a forage harvester provides higher density material than a sugar cane harvester, thereby allowing for more efficient transportation of the harvested material. In one embodiment, using a forage harvester results in harvested sorghum with a bulk density of about 400 kg/m$^3$, compared to sugarcane harvested with a sugarcane harvester with density of about 300 kg/m$^3$, and for sorghum harvested with a sugarcane harvester with a density of about 200 kg/m$^3$. In general, higher bulk density material is cheaper to transport, which tends to limit the geographical area in which cane-harvested crop can be sourced.

Thus, a forage harvester is an overall less expensive way to harvest the selected biomass, such as sorghum, than a cane harvester or dry baled system. Not to be bound by theory, it is believed the cost savings are due in part to higher material throughputs and the higher bulk density of the solid biomass harvested by a forage harvester. The solid biomass can be cut in any length. In one embodiment, the chop lengths of the harvester can be set to a range of about 3 mm to about 80 mm, preferably about 3 mm to about 20 mm, with examples of about 3 mm to about 13 mm chop lengths being most preferred. At these preferred chop lengths, there was not observable aqueous discharge in the forage harvester, so losses were minimal. When a chop length is selected, the harvester provides biomass with an average size or length distribution of about the chop length selected. In one embodiment, the average size distribution of the solid component exiting the recovery system can be adjusted as desired, which can be done by adjusting the chop length of the harvester.

At least one additive is added to the solid biomass to facilitate and/or expedite the conversion of appropriate carbohydrates into volatile organic compounds. After selected additive(s) have been added, the solid biomass can be referred to as prepared biomass material. In one embodiment, the prepared biomass material can comprise at least one or any combination of fermentable sugar-producing plants listed above. In a preferred embodiment, the selected additive(s) can be conveniently added using the harvester during harvest.

In one embodiment, at least about 700 tons, preferably at least about 1 million tons, such as at least 1.2 million tons, or more preferably about at least 5 million tons of prepared biomass material is generated in a particular harvest window based on the growing conditions of a specific region, such as about 1 to 7 months in North America for sorghum.

The at least one additive can be added at any point during and/or after the harvest process. In a preferred embodiment using a forage harvester, additives are added to the solid biomass during the harvest process to generate a prepared biomass material. In particular, forage harvesters are designed for efficiently adding both solid and liquid additives during harvest. As mentioned above, the additives added include at least a microbe (e.g. a yeast), and optionally, an acid and/or an enzyme. In a preferred embodiment, the selected additive(s) are added as solutions. Additional details of the potential additives are further provided below.

For embodiments using a forage harvester or a similar equipment, the selected additive(s) can be added during harvest at all phases, such as before the intake feed rollers, during intake, at chopping, after chopping, through the blower, after the blower, in the accelerator, in the boom (or spout), and/or after the boom. In one embodiment where acid and enzyme are added, the acid is added near the intake feed rollers, and a microbe and the enzyme are added in the boom. In a particular embodiment, a Krone Big X forage harvester with a V12 motor with an about 30 ft wide header is used. In an embodiment using the Krone system, the acid is added as a solution through flexible tubing that discharged the solution just in front of the feed rollers. In this way, the liquid flow can be visually monitored, which showed the acid solution and solid biomass quickly mixed inside the chopping chamber. In another embodiment, the addition of acid was also demonstrated as a viable practice using a Case New Holland FX 58 forage harvester. In certain embodiments, the forage harvester used can include an onboard rack for containing additives, at least the one(s) selected to be added during harvest. In another embodiment, the selected additive(s) to be added during harvest may be towed behind the harvester on a trailer. For example, in one embodiment, it was demonstrated that a modified utility trailer equipped with tanks containing additive solutions of yeast, enzymes and acid can be employed with minimal interfering with normal operations of the harvester, thereby substantially maintaining the expected cost and duration of the harvest process. For example, a normal harvest configuration and biomass yield employing a silage harvester travelling at about 4 miles per hour maintains a similar rate of collection of about 4 miles per hour when equipped with certain additives as described above in one embodiment.

In embodiments of the present invention, the prepared biomass material is eventually transported to a storage facility where it is stored for a period of time to allow for production of at least one volatile organic compound from at least a portion of the fermentable sugar of the solid biomass. The details of the storage phase are further provided below. In certain embodiments, selected additive(s) can also be added at the storage facility. For example, in one embodiment, the selected additive(s) can be added during unloading or after the solid biomass has been unloaded at the storage facility. In one embodiment, a conveyance system is used to assist with the adding of selected additive(s) at the storage facility. Additive(s) added at the storage facility to solid biomass can be one(s) that have not been added or additional amount of one(s) previously added. Accordingly, selected additive(s) can therefore be added at any point from the start of the harvest process to prior to storage of the prepared biomass material at the storage area or facility, such as at points where the material is transferred.

As mentioned above, additive(s) for embodiments of the present invention include at least a microbe and optionally, an acid and/or an enzyme. Selected additive(s) can be added to the solid biomass in any order. In a preferred embodiment, an acid is added to the solid biomass before adding a microbe to prime the material to provide an attractive growth environment for the microbe.

In a preferred embodiment, acid is added to reduce the pH of the solid biomass to a range that facilitates and/or expedites selected indigenous or added microbial growth, which increases production of ethanol and/or volatile organic compounds. The acid can also stop or slow plant respiration, which consumes fermentable sugars intended for subsequent VOC production. In one embodiment, acid is added until the pH of the solid biomass is between about 2.5 and about 5.0, preferably in a range of about 3.7 to about 4.3, and more preferably about 4.2. The acid used can include known acids, such as sulfuric acid, formic acid, or phosphoric acid. The following Table 2 provides non-limiting examples of an acid that can be used individually or in combination.

TABLE 2

| Sulfuric Acid | Formic Acid | Propionic Acid | Malic Acid |
| Phosphoric Acid | Maleic Acid | Folic Acid | Citric Acid |

In a preferred embodiment, after the solid biomass has reached the desired pH with the addition of acid, a microbe is added. A microbe in the additive context refers at least to a living organism added to the solid biomass that is capable of impacting or affecting the prepared biomass material. One exemplary impact or effect from added microbe(s) includes providing fermentation or other metabolism to convert fermentable sugars from various sources, including cellulosic material, into ethanol or other volatile organic compounds. Another exemplary impact or effect may be production of certain enzyme(s) that help to deconstruct cellulose in the prepared biomass material into fermentable sugars which can be metabolized to ethanol or other VOC. Yet another exemplary impact or effect provided by a microbe includes production of compounds such as vitamins, co-factors, and proteins that can improve the quality, and thus value, of an eventual by-product that can serve as feed for animals. Further, microbial activity provides heat for the pile. Parts of the microbial cell walls or other catabolite or anabolite may also offer value-added chemicals that may be recovered by a recovery unit. These impacts and effects may also be provided by microbes indigenous to the solid biomass.

Any microbe that is capable of impacting or affecting the prepared biomass material can be added. In a preferred embodiment, the microbe(s) can include microbes used in the silage, animal feed, wine, and industrial ethanol fermentation applications. In one embodiment, the microbe selected includes yeast, fungi, and bacteria according to application and the desired profile of the organic molecule to be made. In a preferred embodiment, yeast is the selected microbe. In another embodiment, bacteria can be added to make lactic acid or acetic acid. Certain fungi can also be added to make these acids. For example, *Acetobacterium acetii* can be added to generate acetic acid; *Lactobacillus, Streptococcus thermophilus* can be added to generate lactic acid; *Actinobacillus succinogenes, Mannheimia succiniciproducens*, and/or *Anaerobiospirillum succiniciproducens* can be added to generate succinic acid; *Clostridium acetobutylicum* can be added to generate acetone and butanol; and/or *Aerobacter aerogenes* can be added to generate butanediol.

The following Table 3 provides non-limiting examples of preferred microbes, which can be used individually or in combination.

TABLE 3

| | | | |
|---|---|---|---|
| Saccharomyces cerevisiae | Saccharomyces japonicas | Saccharomyces bayanus | Saccharomyces fermentatti |
| Saccharomyces exiguous | Saccharomyces chevalieri | Clostridium acetobutylicum | Clostridium amylosaccharobutylpropylicum |
| Clostridium propylbutylicum | Clostridium viscifaciens | Clostridium propionicum | Aerobacter species |
| Aerobacter aerogenes | Zymomonas mobilis | Zymomonas species | Clostridium species |
| Saccharomyces species | Bacillus species | Clostridium thermocellum | Lactobacillus buchneri |
| Lactobacillus plantarum | Enterococcus faecium | Pediococcus species | Propionibacteria |
| Acetobacterium acetii | Streptococcus thermophilus | Lactobacillus paracasei | Lactobacillus species |
| Actinobacillus succinogenes | Mannheimia succiniciproducens | Anaerobiospirillum succiniciproducens | |

Preferred microbes also include *Saccharomyces cerevisiae* strains that can tolerate high ethanol concentrations and are strong competitors in its respective microbial community. The microbes may be mesophiles or thermophiles. Thermophiles are organisms that grow best at temperatures above about 45° C., and are found in all three domains of life: Bacteria, Archaea and Eukarya. Mesophiles generally are active between about 20° C. and 45° C. In an embodiment using a strain of *Saccharomyces cerevisiae*, the strain can come from a commercially available source such as Biosaf from Lesaffre, Ethanol Red from Phibro, and Lallamand activated liquid yeast. If the microbe is obtained from a commercial source, the microbe can be added according to the recommended rate of the provider, which is typically based on the expected sugar content per wet ton, where water is included in the mass calculation. The term "wet ton" refers at least to the mass unit including water. The recommended amount can be adjusted according to reaction conditions. The microbe added can comprise one strain or multiple strains of a particular microbe. In one embodiment, the microbes are added at a rate of up to 500 mL per wet ton of solid biomass. In a particular embodiment using commercially available yeast, about 300 mL of Lallamand yeast preparation is added per wet ton of solid biomass. In another embodiment, an additional yeast strain can be added. For example, Ethanol Red can be added at a rate between about 0.001 kg/wet ton to about 0.5 kg/wet ton, particularly about 0.1 kg/wet ton. In yet another embodiment, another yeast strain can be added, e.g., Biosaf, at a rate between about 0.001 kg/wet tone to about 0.5 kg/wet ton, particularly about 0.1 kg/wet ton. It is understood that other amounts of any yeast strain can be added. For example, about 10%, about 20%, about 30%, about 40%, about 50%, about 60%, about 70%, about 80%, about 90%, about 1.5 times, about 2 times, about 2.5 times, or about 3 times of the provided amounts of microbes can be added.

In certain embodiments, an enzyme is further added. The enzyme can be one that assists in the generation of fermentable sugars from plant materials that are more difficult for the microbe to metabolize, such as different cellulosic materials, and/or to improve the value of an eventual by-product serving as animal feed, such as by making the feed more digestible. The enzyme can also be an antibiotic, such as a lysozyme as discussed further below. The enzyme added can include one type of enzyme or many types of enzymes. The enzyme can come from commercially available enzyme preparations. Non-limiting examples of enzymes that assist in converting certain difficult to metabolize plant materials into fermentable sugars include cellulases, hemicellulases, ferulic acid esterases, and/or proteases. Additional examples also include other enzymes that either provide or assist the provision for the production of fermentable sugars from the feedstock, or increase the value of the eventual feed by-product.

In certain embodiments, the enzymes that assist in converting certain difficult to metabolize plant materials into fermentable sugars can be produced by the plant itself, e.g. in-plantae. Examples of plants that can produce cellulases, hemicellulases, and other plant-polymer degrading enzymes may be produced within the growing plants are described in the patent publications and patent WO2011057159, WO2007100897, WO9811235, and U.S. Pat. No. 6,818,803, which show that enzymes for depolymerizing plant cell walls may be produced in plants. In another embodiment, ensilagement can be used to activate such plant produced enzymes as well as temper the biomass for further processing. One example is described in patent publication WO201096510. If used, such transgenic plants can be included in the harvest in any amount. For example, certain embodiments may employ in-plantae enzymes produced in plants by using particular transgenic plants exclusively as a feedstock, or incorporating the transgenic plants in an interspersed manner within like or different crops.

In certain embodiments that include such plant-polymer degrading enzymes, ethanol can be produced from cellulosic fractions of the plant. In a particular embodiment, when Novazymes CTEC2 enzyme was added to a sorghum storage system in excess of the recommended amount, about 100 times more than the recommended amount, about 152% of the theoretical ethanol conversion efficiency based on the initial free sugar content was achieved. While such an amount of enzymes can be added using commercially available formulations, doing so can be costly. On the other hand, such an amount of enzymes can be obtained in a more cost effective manner by growing transgenic plants that produce these enzymes at least interspersingly among the biomass crop.

The ethanol production from cellulose occurred during the storage phase, e.g., in silage and was stable for about 102 days of storage, after which the experiment was terminated. This demonstrates that, under the conditions of that particular experiment, an excess of such enzyme activity results in at least about 52% production of ethanol using fermentable sugars from cellulose. Not intended to be bound by theory, for certain embodiments, the immediate addition of acid during harvest in the experiment may have lowered the pH, thereby potentially inducing the enzyme activity, which otherwise could damage the plants if produced while the plants were still growing.

In a preferred embodiment, if an enzyme is added, the enzyme can be any family of cellulase preparations. In one embodiment, the cellulose preparation used is Novozymes Cellic CTec 2 or CTec 3. In another embodiment, a fibrolytic enzyme preparation is used, particularly, Liquicell 2500. If used, the amount of enzyme added to degrade plant polymer can be any amount that achieves the desired conversion of plant material to fermentable sugar, such as the recommended amount. In a particular embodiment, about 80,000 FPU to about 90,000,000 FPU, preferably about 400,000 FPU to about 45,000,000 FPU, more preferably about 800,000 FPU to about 10,000,000 FPU of enzyme is added per wet ton of biomass. The term "FPU" refers to Filter Paper Unit, which refers at least to the amount of enzyme required to liberate 2 mg of reducing sugar (e.g., glucose) from a 50 mg piece of Whatman No. 1 filter paper in 1 hour at 50° C. at approximately pH 4.8.

In certain other embodiments, selected additive(s) added can include other substances capable of slowing or controlling bacterial growth. Non-limiting examples of these other substances include antibiotics (including antibiotic enzymes), such as Lysovin (lysozyme) and Lactrol® (Virginiamycin, a bacterial inhibitor). Control of bacterial growth can allow the appropriate microbe to expedite and/or provide the production of volatile organic compounds. Antibiotic is a general term for something which suppresses or kills life. An example of an antibiotic is a bacterial inhibitor. In one embodiment, a selective antibiotic that is intended to impact bacteria and not other microbes is used. One example of a selective antibiotic is Lactrol, which affects bacteria but does not affect yeasts.

In a particular embodiment, if used, Lactrol can be added at rates of about 1 to 20 part-per-million (ppm) w/v (weight Lactrol per volume liquid) as dissolved in the water phase of the prepared biomass material, for example at about at about 5 ppm w/v. In an embodiment using an enzyme to control bacterial growth, lysozyme is preferably used. The lysozyme can come from a commercial source. An exemplary commercially available lysozyme preparation is Lysovin, which is a preparation of the enzyme lysozyme that has been declared permissible for use in food, such as wine.

The enzyme and/or other antibiotic material, if used, can be added independently or in conjunction with one another and/or with the microbe. In certain embodiments, other compounds serving as nutrients to the microbes facilitating and/or providing the volatile organic compound production can also be added as an additive. The following Table 4 provides non-limiting examples of other substances, including antibiotics, which can be added to the solid biomass.

TABLE 4

| Potassium Metabisulfite | Potassium Bicarbonate | FermaSure ® (from Dupont ™)—oxychlorine products including chlorite | Lysovin |
|---|---|---|---|
| Thiamin | Magnesium Sulfate | Calcium Pantothenate | Diammonium Phosphate |
| Ammonia | Antibiotics | Lactrol | Biotin |

Yeasts and other microbes that are attached to solids individually, as small aggregates, or biofilms have been shown to have increased tolerance to inhibitory compounds. Not intended to be bound by theory, part of the long-term fermentation may be possible or enhanced by such microbial-to-solids binding. As such, the prepared biomass material that includes the microbe optimized for microbial binding as well as additives that may bind microorganisms can experience a greater extent of fermentation and or efficiency of fermentation. Substances providing and/or facilitating long term fermentation is different from substances that increase the rate of fermentation. In certain embodiments, an increase in the rate of fermentation is not as an important factor as the long-term fermentation, particularly over a period of many weeks or months.

The following provides particular amounts of additives applied to one specific embodiment. If used, the rate and amount of adding an acid varies with the buffering capacity of the particular solid biomass to which the particular acid is added. In a particular embodiment using sulfuric acid, 9.3% w/w sulfuric acid is added at rates of up to about 10 liter/ton wet biomass, for example at about 3.8 liter/ton wet biomass to achieve a pH of about 4.2. In other embodiments, the rate will vary depending on the concentration and type of acid, liquid and other content and buffering capacity of the particular solid biomass, and/or desired pH. In this particular embodiment, Lactrol is added at a rate of about 3.2 g/wet ton of solid biomass. Yeasts or other microbes are added according to the recommended rate from the provider, such as according to the expected sugar content per wet ton. In one particular embodiment, Lallemand stabilized liquid yeast is added at about 18 fl oz per wet ton, and Novozymes Cellic CTec2 is added at about 20 fl oz per wet ton.

In a preferred embodiment, selected additive(s) are added to the solid biomass stream during harvest according to aspects of the invention described above to generate the prepared biomass material. Preferably, the prepared biomass material is transported to a storage facility to allow for conversion of carbohydrates of the prepared biomass material into volatile organic compounds of the desired amount and/or await recovery of the volatile organic compounds. Any suitable transportation method and/or device can be used, such as vehicles, trains, etc, and any suitable method to place the prepared biomass material onto the transportation means. Non-limiting examples of vehicles that can be used to transport the biomass material include end-unloading dump trucks, side-unloading dump trucks, and self-unloading silage trucks. In a preferred embodiment, a silage truck is used. In embodiments using a forage harvester to collect the biomass, transportation of such solid biomass is more efficient than transportation of materials collected by conventional means, such as sugar cane billets, because the bulk density is higher in the solid biomass cut with a forage harvester. That is, materials chopped into smaller pieces pack more densely than materials in billets. In one embodiment, the range of bulk densities in a silage truck varies between about 150 kg/m$^3$ and about 350 kg/m$^3$, for example about 256 kg/m$^3$. Because in certain embodiments, all selected additives are added during harvest, preferably on the harvester, the microbe may begin to interact with the biomass during transportation, and in this way transportation is not detrimental to the overall process.

The biomass, whether prepared or not, is delivered to at least one storage area or facility. The storage facility can be located any distance from the harvest site. Selected additive(s) can be added if they have not been added already or if additional amounts or types need to be further added to generate the prepared biomass material. In a preferred embodiment, the prepared biomass is stored in at least one pile on a prepared surface for a period of time. The facility can incorporate man-made or natural topography. Man-made structures can include existing structures at the site not initially designated for silage, such as canals and water treatment ponds. Non-limiting examples of a prepared surface includes a concrete, asphalt, fly ash, or soil surface. The at least one pile can have any dimension or shape, which can depend on operating conditions, such as space available, amount of biomass, desired storage duration, etc.

The conversion process of fermentable sugars is an exothermic reaction. Too much heat, however, can be detrimental to the conversion process if the temperature is in the lethal range for the microbes in the prepared biomass material. However, in an embodiment using about 700 wet tons of biomass and piling up to about 12 feet, ethanol production and stability were satisfactory. Therefore larger piles will likely not suffer from overheating. In one embodiment, an inner portion of the pile maintains a temperature in a range of about 20° C. to about 60° C. for microbes of all types, including thermophiles. In an embodiment not employing thermophiles, an inner portion of the pile maintains a temperature in a range of about 35° C. to about 45° C.

The prepared biomass material that is stored as at least one pile at the storage facility can also be referred to as a wet stored biomass aggregate. After addition of the selected additive(s), at least a portion of the solid biomass is converted to volatile organic compounds, such as fermentation of sugars into ethanol. In one embodiment, the prepared biomass material is stored for a period of time sufficient to achieve an anaerobiasis environment. In a preferred embodiment, the anaerobiasis environment is achieved in about 24 hours. In another embodiment, the anaerobiasis environment is achieved in more than about 4 hours. In yet another embodiment, the anaerobiasis environment is achieved in up to about 72 hours.

The pile can be free standing or formed in another structure, such as a silage bunker, designed to accept silage, including provisions to collect aqueous runoff and leachate, placement of a tarp over the biomass, and to facilitate both efficient initial silage truck unloading into the bunker as well as removal of the biomass year around. The individual bunkers may be sized at about the size to support annual feedstock requirements of about 700 wet tons to 10,000,000 wet tons or more. For example, the storage facility may have 50 bunkers, where each individual bunker can accept 100,000 wet tons of prepared biomass material for a total of a maximum of about 5 million wet tons of stored material at any one time. In a preferred embodiment where ethanol is the volatile organic compound of choice, about 14 gallons to about 16 gallons of ethanol is recovered per one wet ton of prepared biomass material. The provided numbers are exemplary and not intended to limit the amount of prepared biomass material a storage facility can accommodate.

In a particular embodiment, the storage pile further includes a leachate collection system. In one embodiment, the collection system is used to remove leachate collected from the storage pile. For example, the leachate collection system can be adapted to remove liquid from the pile at certain points during the storage period. In another embodiment, the leachate collection system is adapted to circulate the liquid in the storage pile. For example, circulation can involve taking at least a portion of the recovered liquid and routing it back to the pile, preferably at or near the top portion. Such recirculation allows for longer retention time of certain portions of the liquids in the pile, even as the recovery phase of the prepared biomass material begins and portions of the non-liquid component of the prepared biomass material are sent to the recovery unit. The longer retention time results in longer microbial reaction time, and hence, higher concentrations of organic volatile compounds, such as ethanol.

Any suitable leachate collection system known to those skilled in the art can be employed as described. In a particular embodiment, the leachate collection system comprises at least one trough along the bottom of the pile, preferably positioned near the middle, of the storage pile or bunker if one is used, where the storage pile is prepared at a grade designed to direct liquid from the prepared biomass material to the trough and out to a desired collection receptacle or routed to other applications.

In another embodiment, the leachate collection system comprises one or more perforated conduits, preferably pipes made of polyvinyl chloride (PVC), that run along the bottom of the pile to allow the liquid collected in the conduits to be directed away from the pile.

In one embodiment, as the prepared biomass material is added to the bunker or laid on top of the prepared surface, a tractor or other heavy implement is driven over the pile repeatedly to facilitate packing. In one embodiment, the packing ranges from about 7 lbs/ft$^3$ to about 50 lbs/ft$^3$ per cubic foot for the prepared biomass material. In a preferred embodiment, the packing is from about 30 lbs/ft$^3$ to about 50 lbs/ft$^3$, particularly about 44 lbs/ft$^3$. In one embodiment, the compacting of the prepared biomass material in a pile facilitates and/or allows an anaerobiasis environment to be achieved in the preferred time periods described above. In another embodiment, after the packing is performed or during the time the packing is being performed, an air impermeable membrane is placed on the pile, typically a fit for purpose plastic tarp. In a particular embodiment, the tarp is placed on the pile as soon as is practical. For instance, the tar is placed on the pile within a 24-hour period.

In one embodiment, the prepared biomass material is stored for at least about 24 hours and preferably at least about 72 hours (or 3 days) to allow for production of volatile organic compounds, such as ethanol. In one embodiment, the prepared biomass material is stored for about three days, preferably ten days, more preferably greater than ten days. In one embodiment, the time period for storage of the prepared biomass is about 1 day to about 700 days, preferably about 10 to 700 days. In another embodiment, the biomass material is stored for up to about three years. In one embodiment, the prepared biomass material is stored for a time period sufficient to allow a conversion efficiency of sugar to at least one volatile organic compound of at least about 95% of the theoretical production efficiency as calculated through a stoichiometric assessment of the relevant biochemical pathway. In another embodiment, the prepared biomass material is stored for a time period sufficient to allow a calculated conversion efficiency of sugar to at least one volatile organic compound of at least about 100%. In yet another embodiment, the prepared biomass material is prepared with certain additives, such as enzymes, that allow a calculated conversion efficiency of sugar to at least one volatile organic compound of up to about 150% of the theoretical value based on the initial amount of available fermentable sugars. Not intended to be bound by theory, it is believed that, at or above 100% efficiency, the volatile organic compound(s) are produced from both the initially available fermentable sugars and fermentable sugars from cellulosic or other polymeric material in the prepared biomass material, which can be achieved by enzymatic hydrolysis or acid hydrolysis facilitated by certain additive(s) applied to the biomass.

The produced volatile organic products, such as ethanol, remain stable in the stored prepared biomass material for the duration of the storage period. In particular, the prepared biomass material can be stored up to 700 days without significant degradation to the volatile organic compounds. "Significant" in this context refers at least to within the margin of error when measuring the amount or concentration of the volatile organic compounds in the prepared biomass material. In one embodiment, the margin of error is 0.5%. It has been demonstrated that ethanol remains stable in the pile after at least about 330 days with no significant ethanol losses observed. This aspect of embodiments of the present invention is important because it provides for at least eight months of stable storage, which enables year-round VOCs production and recovery with a harvest window of only about four months. Embodiments of the invention provide significant advantages over the conventional just-in-time processing that would only be able to operate during the four months harvest window per year. That is, embodiments of the invention allow a plant to operate year-round using only a four-month harvest window, thereby reducing capitals cost for a plant of the same size as one used for just-in-time processing.

Also, in an embodiment employing a tarp, it is envisioned that placing soil or other medium around and on the tarp edges to 1) provide weight for holding the tarp down; and also 2) to act as a biofilter of the off-gas from the pile. In such an embodiment, biofilters are efficient for organics and carbon monoxide detoxification/degradation. The prepared biomass material can also be stored as compressed modules, drive over piles, bunkers, silos, bags, tubes, or wrapped bales or other anaerobic storage system.

In one embodiment, the off-gas stream from a pile of prepared biomass material was monitored, and it was found that only small levels of organics, and also very low levels of nitrogen oxides, were present. For example, Tables 5.1, 5.2, and 5.3 below show the analysis of various off-gas samples collected during the storage phase of one implementation of certain embodiments of the invention. The designation "BDL" refers to an amount below detectable limit. Summa and Tedlar refer to gas sampling containers commercially available.

TABLE 5.1

| Container type | Container ID | % $H_2$ | % $O_2$ | % $N_2$ | % $CH_4$ | % $CO_2$ | % $H_2O$ | Normalized $CO2$ |
|---|---|---|---|---|---|---|---|---|
| Tedlar bag | A | BDL | 1.72 | 7.84 | BDL | 95.90 | 5.23 | 85.21 |
| Tedlar bag | B | BDL | 2.30 | 9.12 | BDL | 89.97 | 5.97 | 82.62 |
| Tedlar bag | C | BDL | 0.71 | 3.57 | BDL | 97.45 | 5.54 | 90.18 |
| Tedlar bag | D | BDL | 0.72 | 3.18 | BDL | 97.50 | 5.97 | 90.14 |
| Tedlar bag | E | BDL | 1.86 | 7.24 | BDL | 91.75 | 7.64 | 83.26 |
| Summa Container | EQ #8 | 0.01 | 5.74 | 22.14 | 0.07 | 73.74 | 5.28 | 66.84 |
| Summa Container | EQ #13 | 0.09 | 3.28 | 12.89 | 0.33 | 84.48 | 5.66 | 78.18 |
| Summa Container | EQ #16 | 0.12 | 3.30 | 13.01 | 0.12 | 84.65 | 4.99 | 78.70 |

TABLE 5.2

| Container type | Container ID | % $O_2$ | ppmv CO | % $CO_2$ | ppmv HC | ppmv NO | ppmv $NO_2$ | ppmv $NO_x$ | ppmv $SO_2$ |
|---|---|---|---|---|---|---|---|---|---|
| Tedlar bag | A | 1.6 | 13 | 72.7 | 104 | 3.8 | 1.90 | 5.70 | BDL |
| Tedlar bag | B | 4.4 | 19 | 66.2 | 739 | 2.5 | 122.90 | 125.40 | 6 |
| Tedlar bag | C | 0.6 | 29 | 75.3 | 158 | 8.9 | 27.20 | 36.10 | 4 |
| Tedlar bag | D | 0.6 | 35 | 75.7 | 222 | 7.9 | 56.50 | 64.40 | 5 |
| Tedlar bag | E | 4.1 | 35 | 66.8 | 423 | 3.0 | 20.30 | 23.90 | 4 |

TABLE 5.3

| Container type | Container ID | ppmv CH2O | ppmv C2H4O | ppmv methanol | ppmv 2-propanol | ppmv ethanol | ppmv propanol |
|---|---|---|---|---|---|---|---|
| Tedlar bag | A | 386 | 870 | 63.4 | 0.593 | 78.5 | BDL |
| Tedlar bag | B | BDL | 1299 | 678 | 0.186 | 1065 | 15.2 |
| Tedlar bag | C | 18.2 | 590 | 89.2 | 2.784 | 171 | 6.098 |
| Tedlar bag | D | BDL | 941 | 170 | 3.031 | 264 | 7.648 |
| Tedlar bag | E | BDL | 819 | 389 | 2.512 | 634 | 11.3 |

Embodiments of the present invention, although relatively uncontained in the bunker, should be environmentally benign. Even so, certain aspects of the present invention fit well with using soil or other media as a biofilter placed around and on the bunkers because the escape of gas from under the tarp is radial in nature. As such, the vapors have a higher amount of surface area in contact with the edges of the pile. In embodiments using a biofilter, vapor phase releases pass through the biofilter (such as soil or compost) placed near the edge mass before entering into the atmosphere. The biofilter retains many potential environmental pollutants and odors released by the storage pile, and it eliminates or greatly reduces the potentially harmful off-gases released from the storage pile.

In one embodiment, the prepared biomass material is stored until it contains no more than about 80 wt % liquid. The prepared biomass material is stored until it contains at least about 4 to about 5% higher than initial content. At this stage, the wet stored biomass aggregate is not considered "beer" yet since it still contains over about 20% solids. In one embodiment, the prepared biomass material is stored until it contains between about 2 wt % and about 50 wt % ethanol, and preferably between about 4 wt % and about 10 wt % ethanol. The balance of the liquid is primarily water but can contain many other organic compounds, such as acetic acid, lactic acid, etc.

Embodiments of the present invention allow the solid biomass to be harvested in a much shorter harvest window than typical sugar cane juicing operations, which allows for 1) a much larger geographic area where the facilities could be placed, 2) harvest of the crop when the crop has its highest yield potential, 3) harvest of the crop at its highest sugar concentration potential, 4) shorter harvest window still economical, and 5) decoupling the need for taking the juice from the biomass for fermentation.

The preparation of the biomass material of embodiments of the invention can also be generally referred to as solid state fermentation.

VOC Recovery

Once the prepared biomass material has been stored for the desired amount of time and/or contains a desired concentration of volatile organic compounds, such as ethanol, it can be routed to the VOC recovery system for recovery of particular volatile organic compounds. The recovery system and storage facility can be located any distance from one another. Embodiments of systems and methods described herein allow flexibility in the geographical location of both and their locations relative to each other. In a particular embodiment, the recovery system is located about 0.5 to about 2 miles from the storage facility. Any suitable method and/or equipment can be used to transfer the prepared biomass material from the storage facility to the recovery system. In one embodiment, a feed hopper is used. In one embodiment, a silage facer, a front end loader or payloader, a sweep auger or other auger system can be used to place the prepared biomass material into the feed hopper. The material can be placed directly into the feed hopper or it can be transferred to by conveyer system, such as belt system. The feed hopper containing the prepared biomass material can then be driven to the recovery system.

The recovery system is solventless and uses a superheated vapor stream to vaporize the liquid in the prepared biomass material into a gas component, which can then be collected. A super-heated vapor is a vapor that is heated above its saturation temperature at the pressure of operation. In a preferred embodiment, after the recovery system reaches steady state, the superheated vapor stream comprises only vapor previously evaporated from the prepared biomass material, so that no other gas is introduced, thereby reducing the risk of combustion of the volatile organic compounds and/or dilution of the recovered product stream of volatile organic compounds. A portion of the vapor is removed as product and the remainder is recycled back for use in transferring heat to fresh incoming prepared biomass material. The remaining solid component is discharged from the system and can have various subsequent uses. The solid component may also be referred to as solid product in certain instances. The super-heated vapor directly contacts the biomass transferring energy and vaporizing the liquid present there. The heat or thermal energy source does not directly contact the prepared biomass material. Thus, the VOC recovery system can also be described as providing "indirect" heat contact.

To provide solventless recovery of volatile organic compounds, the recovery system comprises a compartment that allows superheated vapor to flow in a continuous manner, i.e., as a stream. In one embodiment, the compartment has a loop shape. In another embodiment, the compartment comprises a rotating drum. The compartment has an inlet through which the prepared biomass material can enter. In one embodiment, the inlet comprises a pressure tight rotary valve, plug screw, or other similar device, which can assist in separating the prepared biomass material to increase the surface area exposed to the superheated vapor stream.

In yet another embodiment, the system further comprises a dewatering mechanism to remove at least a portion of the liquid in the prepared biomass material before the liquid is vaporized. The liquid removal can occur before and/or while the prepared biomass material enters the compartment. The liquid from the prepared biomass material contains at least one volatile organic compound, which can be recovered by further processing the liquid, such as feeding the liquid to a distillation column. The liquid can be routed directly to further processing unit, such as a distillation column. Alternatively or in addition to, the system further includes a collection unit to collect the liquid removed from the prepared biomass material. Any portion of the collected liquid can then be further processed.

In one embodiment, the dewatering mechanism comprises a component adapted to squeeze the liquid from the prepared biomass material. In such an embodiment, the squeezing can be performed while the prepared biomass material is being fed into the compartment. For instance, the inlet can comprise a squeezing mechanism to squeeze liquid from the prepared biomass material as it is introduced into the compartment. Alternatively or in addition to, the squeezing can be performed separately before the prepared biomass material enters the compartment. A non-limiting example of such a squeezing mechanism is a screw plug feeder.

In one embodiment, the liquid removal mechanism comprises a mechanical press. Non-limiting examples of types of mechanical presses include belt filter presses, V-type presses, ring presses, screw presses and drum presses. In a particular embodiment of a belt filter press, the prepared biomass material is sandwiched between two porous belts, which are passed over and under rollers to squeeze moisture out. In another particular embodiment, a drum press comprises a perforated drum with a revolving press roll inside it that presses material against the perforated drum. In yet another embodiment, in a bowl centrifuge, the material enters a conical, spinning bowl in which solids accumulate on the perimeter.

The compartment provides a space where the superheated vapor stream can contact the prepared biomass material to vaporize the liquid from the prepared biomass material. The vaporization of at least a portion of the liquid provides a gas component and a solid component of the prepared biomass material. The system further comprises a separating unit where the solid component of the prepared biomass material can be separated from the gas component, so each component can be removed as desired for further processing. In one embodiment, the separating unit comprises a centrifugal collector. An example of such centrifugal collector is high efficiency cyclone equipment. In a preferred embodiment, the separating unit also serves as an outlet for the solid component. For example, the separating unit can discharge the solid component from the solventless recovery system. There is a separate outlet for the gas component where it can exit the system for further processing, such as distillation. In one embodiment, the separating unit is further coupled to a second pressure tight rotary valve or the like to extrude or discharge the solid component. In one embodiment, the superheated vapor is maintained at a desired temperature above its saturation temperature by a heat exchange component coupled to a heat source where the superheated vapor does not contact the heat source. The heat transfer between the heat source and the system occurs via convection to the superheated vapor. In one embodiment, the heat source can include electrical elements or hot vapors through an appropriate heat exchanger. In one embodiment, the operating pressure is in a range from about 1 psig to about 120 psig. In a preferred embodiment, the operating pressure is in a range from about 3 psig to about 40 psig. In a particularly preferred embodiment, the system is pressurized at an operating pressure of about 60 psig to force the vapor component from the system.

In one embodiment, at start up of the recovery system, the prepared biomass material is introduced into the compartment via the inlet. Steam is initially used as the superheated vapor to initially vaporize the liquid in the prepared biomass material. The superheated vapor continuously moves through the compartment. When the prepared biomass material enters the superheated vapor stream, it becomes fluidized where it flows through the compartment like a fluid. As the prepared biomass material is introduced, it comes into contact with the superheated vapor stream. Heat from the superheated vapor is transferred to the prepared biomass material and vaporizes at least a portion of the liquid in the prepared biomass material and is separated from the solid component, which may still contain moisture. The gas component contains volatile organic compound(s) produced in the prepared biomass material. In a preferred embodiment, as liquid from the prepared biomass material begins to vaporize, at least a portion of the vaporized liquid can be recycled in the system as superheated fluid. That is, during any one cycle, at least a portion of the vaporized liquid remains in the compartment to serve as superheated vapor instead of being collected for further processing, until the next cycle where more prepared biomass material is fed into the system.

In a preferred embodiment, during the initial start up procedure, the superheated fluid can be purged as needed, preferably continuously (intermittently or constantly), until steady state is achieved where the superheated vapor comprises only vaporized liquid of the prepared biomass material. The gas component and solid component can be collected via the respective outlet. Heat can be added continuously (intermittently or constantly) to the system via the heat exchanger coupled to the heat source to maintain the temperature of the superheated vapor, to maintain a desired or target operating pressure in the system, or to maintain a target vaporization rate. Various conditions of the system, such as flow rate of the superheated vapor stream, pressure, and temperature, can be adjusted to achieve the desired liquid and/or volatile organic compounds removal rate.

In one embodiment, the collected gas component is condensed for further processing, such as being transferred to a purification process to obtain a higher concentration of the volatile organic compound(s) of choice. In a preferred embodiment, the collected gas component is fed directly into a distillation column, which provides savings of energy not used to condense the gas component. In another embodiment, the gas component is condensed and fed to the next purification step as liquid.

In one embodiment, before entering the recovery phase, the prepared biomass material has an initial liquid content of about at least 10 wt % and up to about 80 wt % based on the biomass material. In a particular embodiment, the initial liquid content is at least about 50 wt % based on the biomass material. In one embodiment, the initial liquid content comprises from about 2 to 50 wt %, and preferably from about 4 to 10 wt % ethanol based on the initial liquid content.

In one embodiment, the solid component collected contains from about 5 wt % to about 70 wt %, and preferably from about 30 wt % to about 50 wt %, liquid depending on the ethanol removal target. In another component, the collected gas component contains between about 1 wt % and about 50 wt % ethanol, preferably between about 4 wt % and about 15 wt % ethanol. In one embodiment, the recovery system recovers from about 50% to about 100% of the volatile organic compounds contained in the prepared biomass material. The residence time of the prepared biomass varies based on a number of factors, including the volatile organic compound removal target. In one embodiment, the residence time of the prepared biomass material in the compartment is in a range of about 1 to about 10 seconds. In one embodiment, the recovery system can be operated between about 0.06 barg and about 16 barg. The term "barg" refers to bar gauge as understood by one of ordinary skill in the art, and 1 bar equals to 0.1 MegaPascal. In one embodiment, the gas in the recovery system has a temperature in a range of about 100° C. to about 375° C., particularly from about 104° C. to about 372° C., and the solid component exiting the system has a temperature of less than about 50° C. The collected solid component can be used in other applications. Non-limiting examples include animal feed, feed for a biomass burner to supply process energy or generate electricity, or further converted to ethanol by means of a cellulosic ethanol process (either re-ferment in a silage pile, or feed to a pretreatment unit for any cellulosic ethanol process) or a feed for any other bio-fuel process requiring ligno-cellulosic biomass.

The operating conditions of the solventless recovery system include at least one of temperature, pressure, flow velocity, and residence time. Any one or combination of these conditions can be controlled to achieve a target or desired removal target, such as the amount of the initial liquid content removed or the amount of the liquid remaining in the separated liquid component exiting the recovery system. In one embodiment, at least one operating condition is controlled to achieve removal of about 10-90 wt %, preferably about 45-65 wt %, and more preferably about 50 wt %, of the initial liquid content.

In a preferred embodiment, increasing the temperature of the system at constant pressure will cause the liquid in the biomass to be vaporized more quickly and thus for a given residence time will cause a higher percentage of the liquid in the biomass to be evaporated. The vapor flow rate exiting the system has to be controlled to match the rate of vaporization of liquid from the biomass in order to achieve steady state and can also be used as a mechanism to control the system pressure. Increasing the system pressure will cause more energy to be stored in the vapor phase in the system which can then be used to aid in further processing or to help move the vapor to the next downstream processing unit. Increasing the biomass residence time in the system causes more heat to be transferred from the vapor phase to the biomass resulting in more liquid being vaporized.

In a specific exemplary embodiment, the recovery system comprises a closed loop pneumatic superheated steam dryer, which can be obtained from commercially available sources. In one embodiment, the closed loop pneumatic superheated steam dryer is an SSD™ model of GEA Barr-Rosin Inc. Other suitable commercially available equipment include the Superheated Steam Processor, SSP™ from GEA Barr-Rosin Inc, the Ring Dryer from several companies including GEA Ban-Rosin Inc. and Dupps; the Airless Dryer from Dupps; the QuadPass™ Rotary Drum Dryer from DuppsEvactherm™, Vacuum Superheated Steam Drying from Eirich; the rotary drum dryer using superheated vapor from Swiss Combi Ecodry; and the airless dryer from Ceramic Drying Systems Ltd.

Still other types of indirect dryers that could serve as the volatile organics recovery unit for this process are batch tray dryers, indirect-contact rotary dryers, rotating batch vacuum dryers, and agitated dryers. The basic principle for these dryers is that they will be enclosed and attached to a vacuum system to remove vapors from the solids as they are generated (also by lowering the pressure with the vacuum the volatiles are removed more easily). The wet solids contact a hot surface such as trays or paddles, the heat is transferred to the wet solids causing the liquids to evaporate so they can be collected in the vacuum system and condensed.

FIG. 1 illustrates an exemplary VOC recovery system and process employing a superheated steam dryer, referenced as system 100. In a particular embodiment, the superheated steam dry can be obtained from GEA Ban-Rosin Inc. In FIG. 1, prepared biomass material 1 containing ethanol and/or other VOCs following solid state fermentation in the silage piles is fed into compartment 3 through input 2. In the particular embodiment shown, input 2 comprises a screw extruder. As shown in FIG. 1, at least a portion of the liquid of the prepared biomass material 1 is removed prior to entering compartment 3. The dewatering mechanism can be a screw plug feeder through which the prepared biomass material 1 passes. At least a portion of the liquid removed from biomass material 1 can be routed directly to distillation step 11 via stream 15 without going through recovery system 100. Optionally, a delumper can be coupled to the output of the dewatering mechanism can be used to facilitate introduction of the dewatered biomass material into compartment 3.

Referring to FIG. 1, recovery system 100 comprises compartment 3, which can be pressurized, shown as a conduit that has an appropriate diameter, length and shape, adapted to provide the desired operating conditions, such as residence time of prepared biomass material 1, heat transfer to the superheated vapor, and operating pressure and temperature. After entering compartment 3, during steady state operation, prepared biomass material 1 contacts superheated vapor flowing through system 100 at a desired temperature and becomes fluidized. As described above, in a preferred embodiment, the superheated vapor, or at least a portion thereof, is vapor component obtained from prepared biomass materials previously fed into system 100 for VOC recovery. The fluidized biomass flows through compartment 3 at a target flow rate and remains in contact with the superheated vapor for a target residence time sufficient to evaporate the desired amount of liquid from prepared biomass material 1. In the embodiment shown, the flow of the superheated vapor and prepared biomass material 1 through system 100 is facilitated by system fan 14. System 100 can have one or more fans. The flow rate or velocity of the superheated vapor and biomass material 1 can be controlled by system fan 14. Biomass material 1 flows through compartment 3 and reaches separating unit 4, which is preferably a cyclone separator, where a vapor component and a solid component of biomass material 1 are separated from each other. As shown, the vapor component is routed away from the solid component via overhead stream 5 and the remaining portion of biomass material 1 is considered a solid component, which is discharged from separating unit 4 as solid component 7, preferably by screw extruder 6. At least a portion of the discharged solid component 7 can be used as animal feed, burner fuel, or biomass feedstock for other bio-fuels processes.

Figure 3:
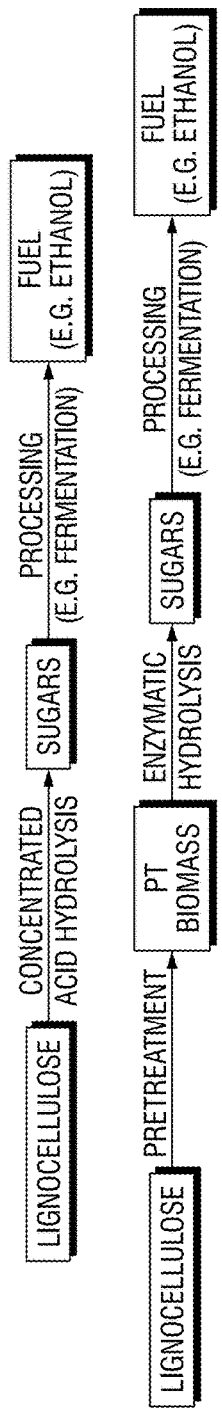
FIG. 3 is a diagram of a particular embodiment for saccharification of a solid component according to certain aspects of the invention.

For example, at least a portion of solid component 7 can serve as feedstock for process 400 that further processes lignocellulosic material contained in solid component 7. Process 400 is illustrated in FIG. 3 and correspondingly further discussed below. Referring to FIG. 1, a portion of the vapor component, referenced as stream 8, is retained and recycled as a portion of the superheated vapor used to vaporize newly introduced prepared biomass material. In the embodiment shown, the retained vapor component in stream 8 is routed through heat exchanger 9 to heat it to the target operating temperature. The heat source can include steam, electricity, hot flue gases or any other applicable heating source known to those skilled in the art.

In a preferred embodiment, the temperature is controlled such that the pressure in the system is maintained at the target and there is adequate energy present to evaporate the desired amount of liquid. The pressure can also be controlled by the flow rate of the superheated vapor stream and the heat input to heat exchanger 9. Preferably, recovery system 100 operates continuously where prepared biomass material 1 is continuously fed at a desired rate, and vapor component 10 and solid component 6 are continuously removed at a continuous rate. In a preferred embodiment, "fresh" vapor component 8 from one run is retained continuously at a target rate to be used as the superheated vapor stream for the next run. Any of these rates are adjustable to achieve the desired operating conditions. As mentioned, system fan 14 circulates the superheated vapor stream through system 100 and can be adjusted to obtain the target flow rate or velocity.

Referring to FIG. 1, the remaining portion of vapor component stream 5, represented as numeral 10 is routed to a distillation step 11. Depending on the distillation configuration, vapor component portion 10 may be condensed before further purification or preferably fed directly into the distillation column as a vapor. In a preferred embodiment, the distillation product from distillation step 11 has an ethanol content of about 95.6 wt % ethanol (the ethanol/water azeotrope), which can further be purified to above about 99 wt % using common ethanol dehydration technology, which is shown as step 12. The final ethanol product 13 will then typically be used as a biofuel for blending with gasoline.

Figure 2:
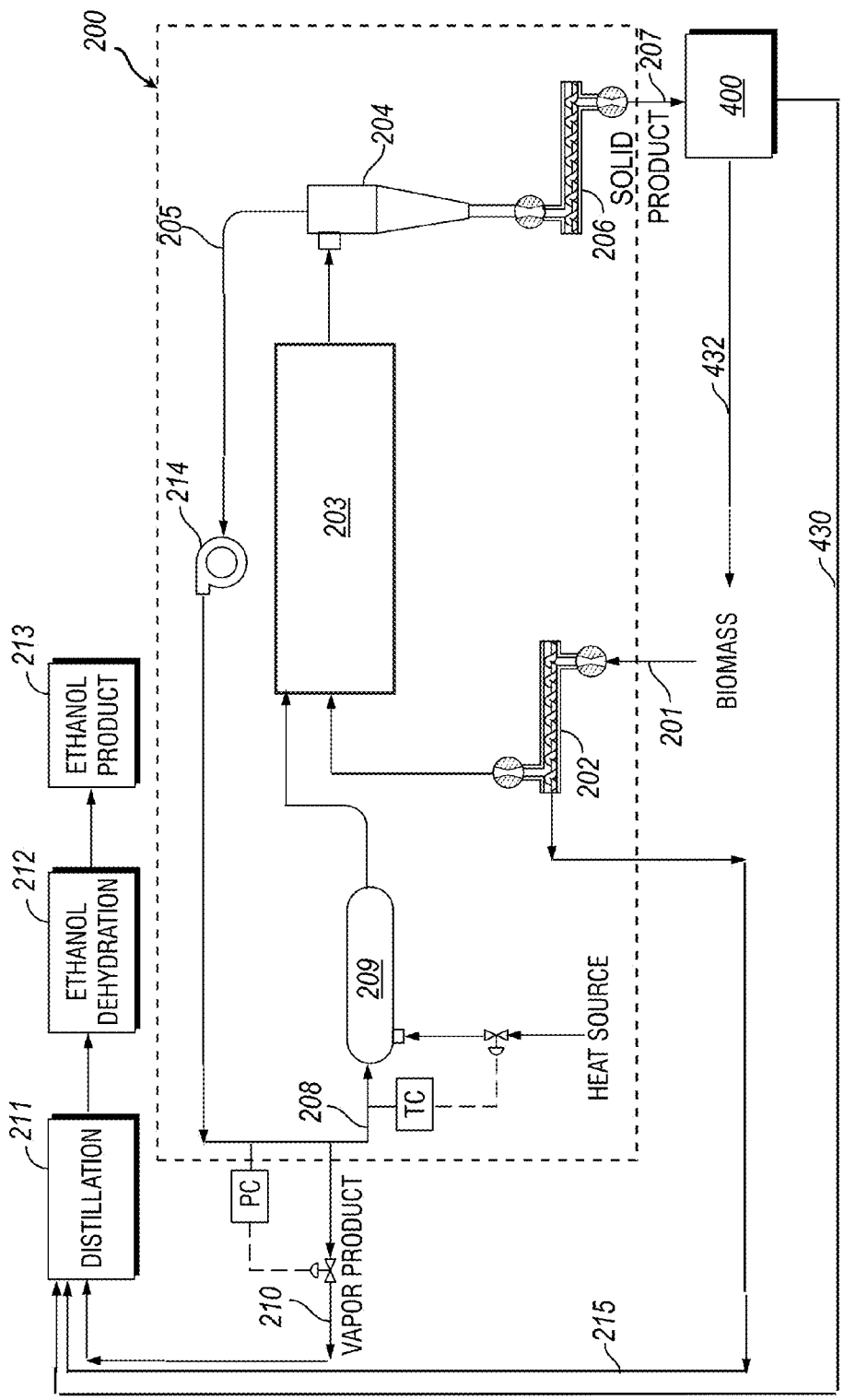
FIG. 2 is a diagram of another embodiment to process biomass material according to certain aspects of the present invention.

FIG. 2 illustrates another exemplary recovery system and process employing a superheated steam dryer, referenced as system 200 that is representative of the Ring Dryer provided by various manufacturers. Prepared biomass material 201 is fed into system 200 through input 202, which preferably comprises a screw extruder. In one embodiment, least a portion of the liquid of the prepared biomass material 201 is removed prior to entering system 200. The dewatering mechanism can be a screw plug feeder through which the prepared biomass material 201 passes. At least a portion of the liquid removed from biomass material 201 can be routed directly to distillation step 211 via stream 215 without going through recovery system 200. Optionally, a delumper can be coupled to the output of the dewatering mechanism can be used to facilitate introduction of the dewatered biomass material into compartment 203.

Referring to FIG. 2, recovery system 200 comprises compartment 203, which preferably comprises a rotating drum that provides the target operating conditions for VOC recovery, including residence time of prepared biomass material 201, heat transfer to the superheated vapor, and operating pressure and temperature. After entering compartment 203, during steady state operation, prepared biomass material 201 contacts superheated vapor flowing through system 200 at the operating temperature and flow rate and becomes fluidized. As described above, in a preferred embodiment, the superheated vapor, or at least a portion thereof, is the vapor component obtained from prepared biomass material previously fed into system 200 for VOC recovery. The fluidized biomass flows through compartment 203 at a target flow rate and remains in contact with the superheated vapor for the target residence time to achieve the target vaporization of liquid from the biomass. The fluidized biomass then reaches separating unit 204, which is preferably a cyclone separator, where the vapor component and solid component are separated from each other. As shown, the vapor component is routed away from the solid component through overhead stream 205, and solid component 207 is discharged from separating unit 204. As shown, solid component 207 exits system 100 via extruder 206 and at least a portion of it can serve as feedstock for process 400, which further processes lignocellulosic material contained in solid component 207. Process 400 is illustrated in FIG. 3 and correspondingly further discussed below. Solid component 207 can be directly routed to process 400. In addition to or alternatively, solid component 207 can be transported to be fed into process 400. A portion of the vapor component, referenced as stream 208, is retained and recycled as a portion of the superheated vapor used to vaporize newly introduced prepared biomass material. As shown, retained vapor component 208 is routed through heat exchanger 209 to heat it to the target or desired temperature. The heat or thermal energy source can include steam, electricity, hot flue gases or any other desired heating source. As shown, hot flue gas is used. The temperature is controlled such that the pressure in the system is maintained at the target and there is adequate energy present to evaporate the desired amount of liquid. The pressure can also be controlled by the flow rate of the superheated vapor stream and the heat input to heat exchanger 209.

Referring to FIG. 2, the remaining portion of vapor component stream 205, represented as numeral 210 is routed to a distillation step. Depending on the distillation configuration, vapor component portion 210 may be condensed before further purification or preferably fed directly into the distillation column as a vapor. The product from the distillation step can further be concentrated using known processes.

Preferably, recovery system 200 operates continuously where prepared biomass material 201 is continuously fed at a desired rate, and vapor component 210 and solid component 206 are continuously removed at a continuous rate. In a preferred embodiment, "fresh" vapor component 208 from one run is retained continuously at a target rate to be used as the superheated vapor stream for the next run. All these rates are adjustable to achieve the desired operating conditions. System fan 214 creates a circulating loop of superheated vapor stream and can be adjusted to obtain the target flow rate.

By using a solventless recovery system according to aspects of the present invention, the points of heat transfer in the system, i.e., addition of heat to the system and heat transfer to the prepared biomass material, take place in the vapor phase in a preferred embodiment, which provides an advantage cause vapor phase heat transfer (convection) is more efficient than solid phase heat transfer (conduction) in the prepared biomass material, which is a bad conductor because it has insulating properties. As mentioned above, in certain embodiments, once steady state is reached no vapor other than that vaporized from the liquid of the prepared biomass material contacts the solid component and gas component of the prepared biomass material in the system, which prevents or reduces dilution that would come from the addition of process steam or other vapor to replenish the superheated vapor stream. The collected gas component can be fed directly to a distillation column for separation of the desired volatile organic compound(s), which can provide significant energy savings. The advantage of this system is that the vapors that contact the wet solids are only those vapors that have been previously removed from the solids so that there is no dilution or explosion risk, etc.

Further Processing of Lignocellulosic Material

Referring to FIGS. 1 and 2, at least a portion of the solid component, such as solid components 7 and component 207, discharged from the recovery system, such as systems 100 and 200, can serve as feedstock to further processing system 400 and be further processed to generate fermentable sugars. The solid component serving as feedstock to further processing system 400 may be referred to as "bio-based feedstock," "solid component feedstock," or "biomass feedstock." Further processing system 400 treats the lignocellulosic material in the solid component to generate fermentable sugars that can be used in subsequent reactions, such as additional fermentation. In a preferred embodiment, the further processing system, such as system 400, is located near the VOC recovery system, such as system 100 or 200, and is coupled to the VOC recovery system so that at least a portion of the solid component discharged from the recovery system is directly routed as feedstock to further processing system 400, which is preferably operated in a continuous or semi-continuous flow mode. In that preferred embodiment, the solid component feedstock is in an entrained engineered system where it is already flowing in an engineered system instead of requiring a mechanism to take it from storage and introduce it to the further processing system. Further, embodiments that couple the VOC recovery system to the further processing system can allow for production of volatile organic compounds from various sources, e.g., readily available fermentable sugars and lignocellulosic material, at one site, which reduces storage, handling, and transportation costs associated with other feedstock sources, which are not already in an entrained system. Such embodiments can also provide a continuous supply of feedstock that is already particle size reduced in contrast to conventional feedstock that often requires storage, transportation, and/or size reduction at or prior to arriving at the facility for additional processing of lignocellulosic material, which reduces the particular associated costs. Alternatively or in addition, the solid component can be transported to other further processing systems located at a different location. The solid component can be pelletized or further formatted to facilitate transport and/or reduce transportation costs. In embodiments of the invention, the solid component is already particle size reduced, which reduces the cost and difficulties of pelletization or other formatting processes as compared to other feedstock sources.

In certain embodiments, the further processing comprises contacting at least a portion of the solid component with a solution adapted to facilitate saccharification. The term "saccharification" has its ordinary meaning, which refers at least to the process of converting a complex carbohydrate (such as starch or cellulose) into simple or fermentable sugars. Any saccharification process or any combination of saccharification process can be used, such as chemical and/or enzymatic. FIG. 3 provides two exemplary saccharification routes for lignocellulosic material: one via concentrated acid hydrolysis and the other via pretreatment and enzymatic hydrolysis. In a preferred embodiment, the saccharification process comprises pretreating the solid component feedstock for subsequent enzymatic hydrolysis. It is understood that the pretreatment of the solid component feedstock can also result in partial or at least some saccharification. Pretreatment is preferred because the lignocellulose is recalcitrant to enzymatic hydrolysis because of its structural complexity. Pretreatment of the solid component feedstock can improve its enzymatic digestibility, typically by removing hemicellulose and making the cellulose more accessible to cellulase enzymes. A variety of chemical and mechanical pretreatment methods are contemplated, including but not limited to, dilute acid, hot-water, ammonia, alkali, SPORL, steam explosion, ionic liquid, organosolv, etc., which, have been well described in the literature (see, e.g. Zhu and Pan (2010), Bioresource Technology, 101: 4992-5002; Hendriks and Zeeman (2009), Bioresource Technology, 100:10-18, the disclosures of both articles are herein incorporated by reference in their entireties for all purposes.)

For example, in one embodiment, pretreatment comprises using hot water in a range from about 170 degrees C. to about 200 degrees C. In another embodiment, pretreatment comprises using a high temperature, dilute-sulfuric acid process, which effectively hydrolyzes the hemicellulosic portion of the biomass to soluble sugars and exposes the cellulose so that enzymatic saccharification can be successful. In one embodiment, the temperature of the pretreatment with the dilute acid solution is in a range from about 140 degrees C. to about 170 degrees C. The parameters which can be employed to control the conditions of the dilute acid pretreatment include time, temperature, and acid loading. These are often combined in a mathematical equation termed the combined severity factor. In general, the higher the acid loading employed, the lower the temperature that can be employed in the pretreatment. Conversely, the lower the temperature used, the longer the pretreatment process takes.

In one embodiment, further processing system 400 further includes subject at least a portion of the pretreated product to enzymatic hydrolysis to generate additional fermentable sugars. Additional information regarding enzymatic hydrolysis is further provided below. In a particular embodiment, the fermentable sugars from further processing of lignocellulosic material can then be fermented using a variety of microbes as described herein; for example, using a microbe adapted to produce a hydrocarbon. This can generally be referred to as lignocellulosic fermentation.

Referring to FIGS. 1 and 2, in one embodiment, at least a portion of liquid from the lignocellulosic fermentation, which contains VOCs, can be routed via stream 430 to join distillation process 11 or 211 of vapor component 10 or 210 and/or liquid product 15 or 215 recovered from prepared biomass 1 or 201 using solventless recovery system 100 or 200 as described above. Likewise, the VOCs in at least a portion of any solid material from the lignocellulosic fermentation in further processing 400 can be recovered using the solventless recovery system 100 or 200, as indicated by stream 432. Accordingly, certain embodiments of the invention can provide for an integrated overall system for generation of VOCs from readily available fermentable sugars in biomass, recovery of those VOCs, processing lignocellulosic material from the first round of fermentation and recovery, generating additional VOCs from lignocellulosic material, and recovery of same. Such a system in those embodiments does not require additional equipment cost, and thus capital investment, where the same equipment can be used for all VOCs production.

In a particularly preferred embodiment, an acid solution comprising at least one alpha-hydroxysulfonic acid is used. The α-hydroxysulfonic acid is effective for hydrolyzing the biomass to fermentable sugars like pentose such as xylose at lower temperature, e.g., about 100° C. for α-hydroxymethane sulfonic acid or α-hydroxyethane sulfonic acid, producing little to no furfural in the process. A portion of the cellulose has also been show to hydrolyze under these comparatively mild conditions. It has been found that other polysaccharides such as starch are also readily hydrolyzed to component sugars by α-hydroxy sulfonic acids. Further, the α-hydroxysulfonic acid is reversible to readily removable and recyclable materials unlike mineral acids such as sulfuric, phosphoric, or hydrochloric acid. The lower temperatures and pressures employed in the biomass treatment leads to lower equipment cost. Biomass pretreated in this manner has been shown to be highly susceptible to additional saccharification, especially enzyme mediated saccharification.

The alpha-hydroxysulfonic acids of the general formula

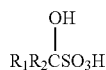

where $R_1$ and $R_2$ are individually hydrogen or hydrocarbyl with up to about 9 carbon atoms that may or may not contain oxygen can be used in the treatment of the instant invention. The alpha-hydroxysulfonic acid can be a mixture of the aforementioned acids. The acid can generally be prepared by reacting at least one carbonyl compound or precursor of carbonyl compound (e.g., trioxane and paraformaldehyde) with sulfur dioxide or precursor of sulfur dioxide (e.g., sulfur and oxidant, or sulfur trioxide and reducing agent) and water according to the following general equation 1.

$R_1=R_2=H$ (formaldehyde)  $R_1=H, R_2=CH_3$ (acetaldehyde)

$R_1=H, R_2=CH_2CH_3$ (propionaldehyde)

$R_1=H, R_2=CH_2CH_2CH_3$ (n-butyraldehyde)

$R_1=H, R_2=CH(CH_3)_2$ (i-butyraldehyde)

$R_1=H, R_2=CH_2OH$ (glycolaldehyde)

$R_1=H, R_2=CHOHCH_2OH$ (glyceraldehdye)

$R1=H, R2=C(=O)H$ (glyoxal)

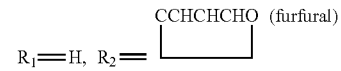

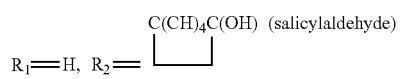

$R_1=R_2=CH_3$ (acetone)  $R_1=CH_2OH, R_2=CH_3$ (acetol)

$R_1=CH_3, R_2=CH_2CH_3$ (methyl ethyl ketone)

$R_1=CH_3, R_2=CHC(CH_3)_2$ (mesityl oxide)

$R_1=CH_3, R_2=CH_2CH(CH_3)_2$ (methyl i-butyl ketone)

$R_1, R_2=(CH_2)_5$ (cyclohexanone) or $R_1=CH_3, R_2=CH_2Cl$ (chloroacetone)

The carbonyl compounds and its precursors can be a mixture of compounds described above. For example, the mixture can be a carbonyl compound or a precursor such as, for example, trioxane which is known to thermally revert to formaldehyde at elevated temperatures or an alcohol that maybe converted to the aldehyde by dehydrogenation of the alcohol to an aldehyde by any known methods. An example of such a conversion to aldehyde from alcohol is described below. An example of a source of carbonyl compounds maybe a mixture of hydroxyacetaldehyde and other aldehydes and ketones produced from fast pyrolysis oil such as described in "Fast Pyrolysis and Bio-oil Upgrading, Biomass-to-Diesel Workshop", Pacific Northwest National Laboratory, Richland, Wash., Sep. 5-6, 2006. The carbonyl compounds and its precursors can also be a mixture of ketones and/or aldehydes with or without alcohols that may be converted to ketones and/or aldehydes, preferably in the range of 1 to 7 carbon atoms.

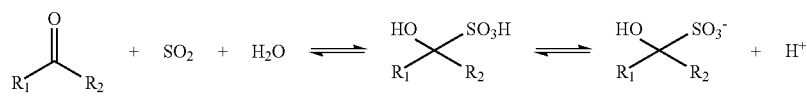

where $R_1$ and $R_2$ are individually hydrogen or hydrocarbyl with up to about 9 carbon atoms or a mixture thereof.

Illustrative examples of carbonyl compounds useful to prepare the alpha-hydroxysulfonic acids include The preparation of alpha-hydroxysulfonic acids by the combination of an organic carbonyl compounds, $SO_2$ and water is a general reaction and is illustrated in equation 2 for acetone.

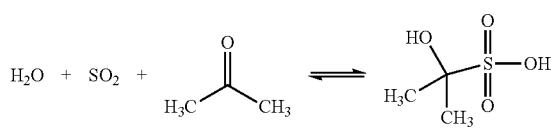

The alpha-hydroxysulfonic acids appear to be as strong as, if not stronger than, HCl since an aqueous solution of the adduct has been reported to react with NaCl freeing the weaker acid, HCl (see U.S. Pat. No. 3,549,319). The reaction in equation 1 is a true equilibrium, which results in facile reversibility of the acid. That is, when heated, the equilibrium shifts towards the starting carbonyl, sulfur dioxide, and water (component form). If the volatile components (e.g. sulfur dioxide) is allowed to depart the reaction mixture via vaporization or other methods, the acid reaction completely reverses and the solution becomes effectively neutral. Thus, by increasing the temperature and/or lowering the pressure, the sulfur dioxide can be driven off and the reaction completely reverses due to Le Châtelier's principle, the fate of the carbonyl compound is dependent upon the nature of the material employed. If the carbonyl is also volatile (e.g. acetaldehyde), this material is also easily removed in the vapor phase. Carbonyl compounds such as benzaldehyde, which are sparingly soluble in water, can form a second organic phase and be separated by mechanical means. Thus, the carbonyl can be removed by conventional means, e.g., continued application of heat and/or vacuum, steam and nitrogen stripping, solvent washing, centrifugation, etc. Therefore, the formation of these acids is reversible in that as the temperature is raised, the sulfur dioxide and/or aldehyde and/or ketone can be flashed from the mixture and condensed or absorbed elsewhere in order to be recycled. It has been found that these reversible acids, which are approximately as strong as strong mineral acids, are effective in biomass treatment reactions. It had been found that these treatment reactions produce very few of the undesired byproducts, furfurals, produced by other conventional mineral acids. Additionally, since the acids are effectively removed from the reaction mixture following treatment, neutralization with base and the formation of salts to complicate downstream processing is substantially avoided. The ability to reverse and recycle these acids also allows the use of higher concentrations than would otherwise be economically or environmentally practical. As a direct result, the temperature employed in biomass treatment can be reduced to diminish the formation of byproducts such as furfural or hydroxymethylfurfural.

It had been found that the position of the equilibrium given in equation 1 at any given temperature and pressure is highly influenced by the nature of the carbonyl compound employed, steric and electronic effects having a strong influence on the thermal stability of the acid. More steric bulk around the carbonyl tending to favor a lower thermal stability of the acid form. Thus, one can tune the strength of the acid and the temperature of facile decomposition by the selection of the appropriate carbonyl compound.

In some embodiments, the reactions described are carried out in any system of suitable design, including systems comprising continuous-flow (such as CSTR and plug flow reactors), batch, semi-batch or multi-system vessels and reactors and packed-bed flow-through reactors. For reasons strictly of economic viability, it is preferable that the invention is practiced using a continuous-flow system at steady-state equilibrium. In one advantage of the process in contrast with the dilute acids pretreatment reactions where residual acid is left in the reaction mixture (<1% wt. sulfuric acid), the lower temperatures employed using these acids (10 to 20% wt.) results in substantially lower pressures in the reactor resulting in potentially less expensive processing systems such as plastic lined reactors, duplex stainless reactors, and 2205 type reactors.

Figure 4:
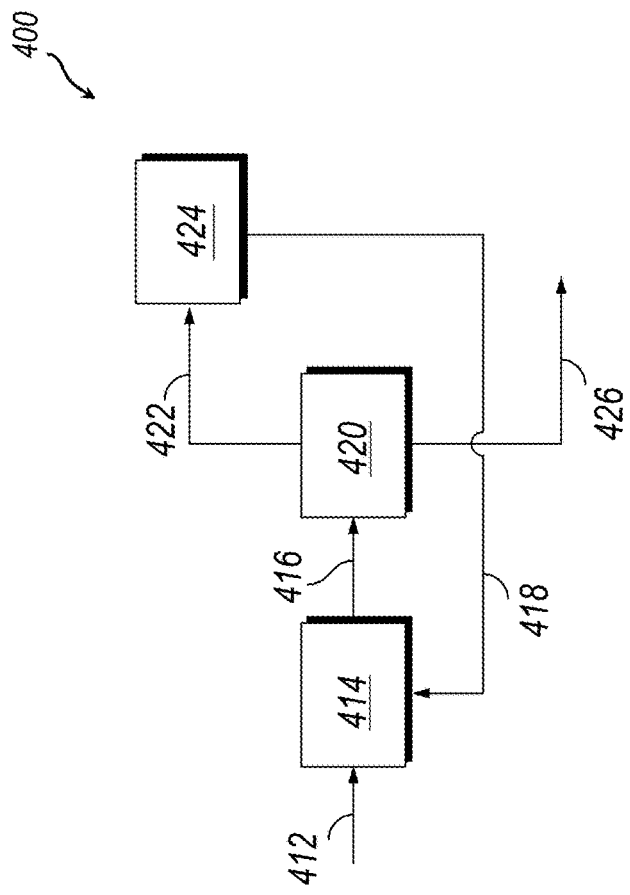
FIG. 4 is a diagram of another embodiment for saccharification of a solid component according to certain aspects of the invention.

FIG. 4 shows an embodiment for converting into sugars the solid component feedstock obtained according to aspects of the invention. In the embodiment shown, feedstock 412 comprises at least a portion of a solid component generated according to aspects of embodiments of the invention, such as solid component 7 or 207 of FIGS. 1 and 2. In this embodiment, biomass feedstock 412 is introduced to a hydrolysis reaction 414 along with a recycle stream 418. The hydrolysis reaction 414 can comprise a number of components including in situ generated α-hydroxysulfonic acid. The term "in situ" as used herein refers to a component that is produced within the overall process; it is not limited to a particular reactor for production or use and is therefore synonymous with an in process generated component. The reacted product stream 416 from 414 is introduced to acid removal system 420 where the acid is removed in its component form then is recovered 422 (and optionally scrubbed 424) and recycled via recycle stream 418 to 414 and product stream 426 containing at least one fermentable sugar (e.g., pentose and optionally hexose) substantially free of the alpha-hydroxysulfonic acids is produced for further processing. The removed acid as components is recycled to 414 as components and/or in its recombined form.

Figure 5:
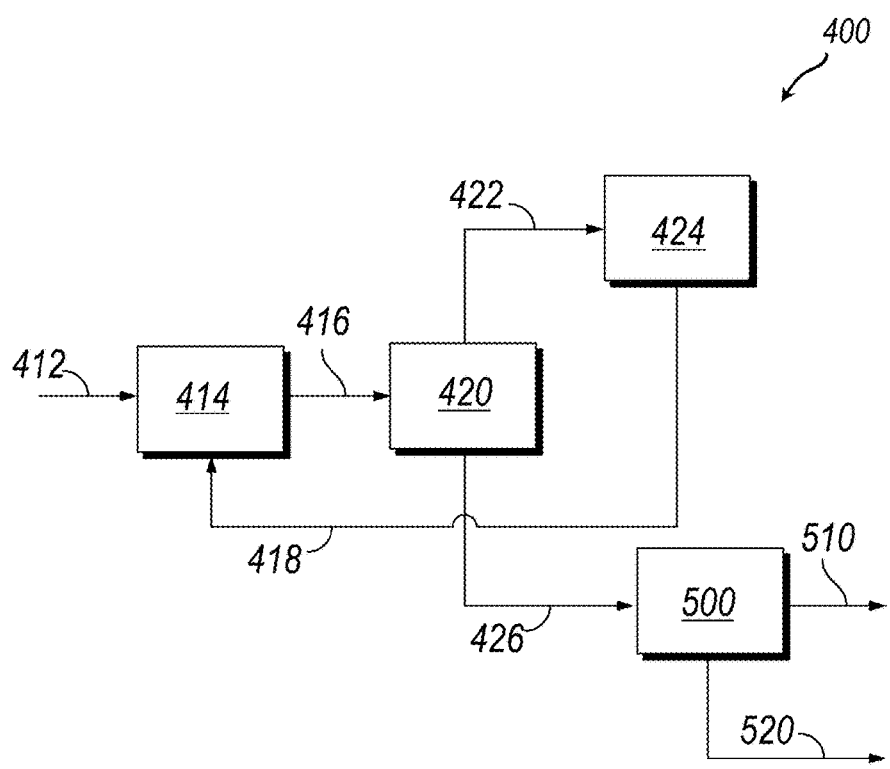
FIG. 5 is a diagram of yet another embodiment for saccharification of a solid component according to certain aspects of the invention.

FIG. 5 shows another embodiment for converting into sugars the solid component feedstock obtained according to aspects of the invention. In the embodiment shown, feedstock 412 comprises at least a portion of a solid component generated according to aspects of embodiments of the invention, such as solid component 7 or 207 of FIGS. 1 and 2. In this embodiment, feedstock 412 is introduced to a hydrolysis reaction 414 along with a recycle stream 418. The hydrolysis reaction 414 can comprise a number of components including in situ generated α-hydroxysulfonic acid. The reacted product stream 416 from 414 is introduced to acid removal system 420 where the acid is removed in its component form then is recovered 422 (and optionally scrubbed 424) and recycled via recycle stream 418 to 414 and product stream 426 containing at least one fermentable sugar (e.g., pentose and optionally hexose) without the alpha-hydroxysulfonic acids is produced. The removed acid as components is recycled to 414 as components and/or in its recombined form. The product stream 426 is filtered at 500 to produce a liquid stream 510 containing fermentable sugar (e.g., pentose and optionally hexose) and a wet solid stream 520 containing cellulose and lignin.

In one embodiment (not shown), at least a portion of product stream 426 and/or wet solid stream 520, can further be subject to enzymatic hydrolysis to generate additional fermentable sugars. Additional information regarding enzymatic hydrolysis is further provided below. In a particular embodiment, the fermentable sugars from further processing of lignocellulosic material (including liquid stream 510) can then be fermented using a variety of microbes as described above to generate a plurality of volatile organic compounds. This can generally be referred to as lignocellulosic fermentation. In one embodiment, at least a portion of liquid from the lignocellulosic fermentation, which contains VOCs, can be routed to join the distillation process of vapor and/or liquid products recovered from the prepared biomass using a solventless recovery system as described above. Likewise, the VOCs in at least a portion of any solid material from the lignocellulosic fermentation can be recovered using the same solventless recovery system that is used to recover VOCs from the prepared biomass material.

Various factors affect the conversion of the biomass feedstock in the hydrolysis reaction. The carbonyl compound or incipient carbonyl compound (such as trioxane)

with sulfur dioxide and water should be added to in an amount and under conditions effective to form alpha-hydroxysulfonic acids. The temperature and pressure of the hydrolysis reaction should be in the range to form alpha-hydroxysulfonic acids and to hydrolyze biomass into fermentable sugars. The amount of carbonyl compound or its precursor and sulfur dioxide should be to produce alpha-hydroxysulfonic acids in the range from about 1 wt %, preferably from about 5 wt %, most preferably from about 10 wt %, to about 55 wt %, preferably to about 50 wt %, more preferably to about 40 wt %, based on the total solution. For the reaction, excess sulfur dioxide is not necessary, but any excess sulfur dioxide may be used to drive the equilibrium in eq. 1 to favor the acid form at elevated temperatures. The contacting conditions of the hydrolysis reaction may be conducted at temperatures preferably at least from about 50° C. depending on the alpha-hydroxysulfonic acid used, although such temperature may be as low as room temperature depending on the acid and the pressure used. The contacting condition of the hydrolysis reaction may range preferably up to and including about 150° C. depending on the alpha-hydroxysulfonic acid used. In a more preferred condition the temperature is at least from about 80° C., most preferably at least about 100° C. In a more preferred condition the temperature range up to and including about 90° C. to about 120° C. The reaction is preferably conducted at as low a pressure as possible, given the requirement of containing the excess sulfur dioxide. The reaction may also be conducted at a pressure as low as about 1 barg, preferably about 4 barg, to about pressure of as high as up to 10 barg The temperature and pressure to be optimally utilized will depend on the particular alpha-hydroxysulfonic acid chosen and optimized based on economic considerations of metallurgy and containment vessels as practiced by those skilled in the art.

The amount of acid solution to "dry weight" biomass determines the ultimate concentration of fermentable sugar obtained. Thus, as high a biomass concentration as possible is desirable. This is balanced by the absorptive nature of biomass with mixing, transport and heat transfer becoming increasingly difficult as the relative amount of biomass solids to liquid is increased. Numerous methods have been utilized by those skilled in the art to circumvent these obstacles to mixing, transport and heat transfer. Thus weight percentage of biomass solids to total liquids (consistency) may be as low as 1% or as high as 33% depending on the apparatus chosen and the nature of the biomass.

The temperature of the hydrolysis reaction can be chosen so that the maximum amount of extractable carbohydrates are hydrolyzed and extracted as fermentable sugar (more preferably pentose and/or hexose) from the biomass feedstock while limiting the formation of degradation products.

In some embodiments, a plurality of reactor vessels may be used to carry out the hydrolysis reaction. These vessels may have any design capable of carrying out a hydrolysis reaction. Suitable reactor vessel designs can include, but are not limited to, batch, trickle bed, co-current, counter-current, stirred tank, or fluidized bed reactors. Staging of reactors can be employed to achieve the optimal or desired economical solution. The remaining biomass feedstock solids may then be optionally separated from the liquid stream to allow more severe processing of the recalcitrant solids or pass directly within the liquid stream to further processing that may include enzymatic hydrolysis, fermentation, extraction, distillation and/or hydrogenation. In another embodiment, a series of reactor vessels may be used with an increasing temperature profile so that a desired sugar fraction is extracted in each vessel. The outlet of each vessel can then be cooled prior to combining the streams, or the streams can be individually fed to the next reaction for conversion.

Suitable reactor designs can include, but are not limited to, a backmixed reactor (e.g., a stirred tank, a bubble column, and/or a jet mixed reactor) may be employed if the viscosity and characteristics of the partially digested bio-based feedstock and liquid reaction media is sufficient to operate in a regime where bio-based feedstock solids are suspended in an excess liquid phase (as opposed to a stacked pile digester). It is also conceivable that a trickle bed reactor could be employed with the biomass present as the stationary phase and a solution of alpha-hydroxysulfonic acid passing over the material.

The treatment reaction product contains fermentable sugar or monosaccharides, such as pentose and/or hexose that is suitable for further processing. The residual alpha-hydroxysulphonic acid can be removed by application of heat and/or vacuum from the fermentable sugar containing product stream to reverse the formation of alpha-hydroxysulphonic acid to its starting material to produce a stream containing fermentable sugar substantially free of the α-hydroxysulfonic acid. In particular, the product stream is substantially free of alpha-hydroxysulphonic acid, meaning no more than about 2 wt % is present in the product stream, preferably no more than about 1 wt %, more preferably no more than about 0.2 wt %, most preferably no more than about 0.1 wt % present in the product stream. The temperature and pressure will depend on the particular alpha-hydroxysulphonic acid used and minimization of temperatures employed are desirable to preserve the sugars obtain in treatment reactions. Typically the removal may be conducted at temperatures in the range from about 50° C., preferably from about 80° C., more preferably from 90° C., to about 110° C., up to about 150° C. The pressure may be in the range of from about 0.5 barg, to about 2 barg, more preferably from 0.1 barg to about 1 barg. It can be appreciated by a person skill in the art that the treatment reaction 414 and the removal of the acid 420 can occurred in the same vessel or a different vessel or in a number of different types of vessels depending on the reactor configuration and staging as long as the system is designed so that the reaction is conducted under condition favorable for the formation and maintainence of the alpha-hydroxysulfonic acid and removal favorable for the reverse reaction (as components). As an example, the reaction in the reactor vessel 414 can be operated at approximately 100° C. and a pressure of 4 barg in the presence of alpha-hydroxyethanesulfonic acid and the removal vessel 420 can be operated at approximately 110° C. and a pressure of 0.5 barg. It is further contemplated that the reversion can be favored by the reactive distillation of the formed alpha-hydroxysulfonic acid. In the recycling of the removed acid, optionally additional carbonyl compounds, $SO_2$, and water may be added as necessary. The removed starting material and/or alpha-hydroxysulphonic acid may be condensed and/or scrubbed by contact with water and recycled to the reaction 414.

Thus, a typical reaction mixture contains (a) a biomass containing polysaccharides, (b) at least one α-hydroxysulfonic acid, and (c) water. Once some of the biomass is hydrolyzed the reaction mixture contains (a) a biomass containing polysaccharides, (b) at least one α-hydroxysulfonic acid (c) water, and (d) at least one fermentable sugar.

In one embodiment, the product stream from any pretreatment process can further be hydrolyzed by other methods, for example by enzymes to further hydrolyze the biomass to sugar products containing pentose and hexose (e.g., glucose) and fermented to produce alcohols such as disclosed in US Publication No. 2009/0061490 and U.S. Pat. No. 7,781,191 which disclosures are hereby incorporated by reference.

In yet another embodiment, the fermentable sugar can be converted to furfural or hydroxymethylfurfural (HMF) or further fermented to alcohols. Although in some embodiments it may be desirable to minimize the formation of furfurals, if formation of furfurals is desired, the acid containing solution of step (b) may be further heated to a temperature in the range of from 110 to 160° C., more preferably in the range of from 420 to 150° C. to form at least one furfural containing product stream. In one embodiment, the temperature of step (b) is maintained to a temperature of 100° C. or less if it is desirable to obtain minimal furfural in the product stream.

In yet another embodiment, the fermentable sugars can be converted to higher hydrocarbons as a biofuel component using catalytic hydrogenation and condensation techniques rather than further hydrolysis by enzyme and fermentation. Typically the fermentable sugar containing product is contacted with hydrogen in the presence of a hydrogenolysis catalyst to form a plurality of oxygenated intermediates, and then further processing the oxygenated intermediates to produce a fuel blend in one or more processing reactions. In an embodiment, a condensation reaction can be used along with other reactions to generate a fuel blend and may be catalyzed by a catalyst comprising acid or basic functional sites, or both to product a liquid fuel. As used herein, the term "higher hydrocarbons" refers to hydrocarbons having an oxygen to carbon ratio less than at least one component of the biomass feedstock. As used herein the term "hydrocarbon" refers to an organic compound comprising primarily hydrogen and carbon atoms, which is also an unsubstituted hydrocarbon. In certain embodiments, the hydrocarbons of the invention also comprise heteroatoms (e.g., oxygen or sulfur) and thus the term "hydrocarbon" may also include substituted hydrocarbons.

In one such example, the fermentable sugar containing product stream may be further processed to produce mixtures of C4+ compounds useful for biofuels such as described in U.S. Publication No. US2011/0154721 and U.S. patent application Ser. No. 13/106,509, filed May 12, 2011 which disclosures are hereby incorporated by reference. As another such example, the fermentable sugar containing product stream may be further processed to produce mixtures of C4+ compounds useful for biofuels such as described in U.S. Publication No. 20080216391, which disclosure is hereby incorporated by reference. The solid feed may also be suitable for use in fast pyrolysis reactions leading to fuels and chemicals.

In an enzymatic hydrolysis-fermentation processes, the pH of the pretreated feedstock to the enzymatic hydrolysis is typically adjusted so that it is within a range which is optimal for the cellulase enzymes used. Generally, the pH of the pretreated feedstock is adjusted to within a range of about 3.0 to about 7.0, or any pH there between.

The temperature of the treated feedstock is adjusted so that it is within the optimum range for the activity of the cellulase enzymes. Generally, a temperature of about 15° C. to about 100° C., about 20° C. to about 85° C., about 30° C. to about 70° C. preferably or any temperature there between, is suitable for most cellulase enzymes. The cellulase enzymes and the β-glucosidase enzyme are added to the pretreated feedstock, prior to, during, or after the adjustment of the temperature and pH of the aqueous slurry after pretreatment. Preferably the cellulase enzymes and the β-glucosidase enzyme are added to the pretreated lignocellulosic feedstock after the adjustment of the temperature and pH of the slurry.

By the term "cellulase enzymes" or "cellulases," it is meant a mixture of enzymes that hydrolyze cellulose. The mixture may include cellobiohydrolases (CBH), glucobiohydrolases (GBH), endoglucanases (EG), and β-glucosidase. By the term "β-glucosidase", it is meant any enzyme that hydrolyzes the glucose dimer, cellobiose, to glucose. In a non-limiting example, a cellulase mixture may include EG, CBH, and β-glucosidase enzymes.

The enzymatic hydrolysis may also be carried out in the presence of one or more xylanase enzymes. Examples of xylanase enzymes that may also be used for this purpose and include, for examples, xylanase 1, 2 (Xyn1 and Xyn2) and β-xylosidase, which are typically present in cellulase mixtures.

The process can be carried out with any type of cellulase enzymes, regardless of their source. Non-limiting examples of cellulases which may be used include those obtained from fungi of the genera *Aspergillus, Humicola,* and *Trichoderma, Myceliophthora, Chrysosporium* and from bacteria of the genera *Bacillus, Thermobifida* and *Thermotoga*. In some embodiments, the filamentous fungal host cell is an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

The cellulase enzyme dosage is chosen to convert the cellulose of the pretreated feedstock to glucose. For example, an appropriate cellulase dosage can be about 0.1 to about 40.0 Filter Paper Unit(s) (FPU or IU) per gram of cellulose, or any amount there between. The term Filter Paper Unit(s) refers to the amount of enzyme required to liberate 2 mg of reducing sugar (e.g., glucose) from a 50 mg piece of Whatman No. 1 filter paper in 1 hour at 50° C. at approximately pH 4.8.

In practice, the hydrolysis may be carried out in a hydrolysis system, which may include a series of hydrolysis reactors. The number of hydrolysis reactors in the system depends on the cost of the reactors, the volume of the aqueous slurry, and other factors. The enzymatic hydrolysis with cellulase enzymes produces an aqueous sugar stream (hydrolyzate) comprising glucose, unconverted cellulose, lignin and other sugar components. The hydrolysis may be carried out in two stages (see U.S. Pat. No. 5,536,325, which is incorporated herein by reference), or may be performed in a single stage.

In one embodiment, the treated solid component comprising fermentable sugars can then be fermented by one or more microorganism to produce a fermentation broth comprising the desired chemical. In the lignocellulosic fermentation system, any one of a number of known microorganisms may be used to convert sugar to the desired fermentation products. The microorganisms can convert at least sugars, including, but not limited to glucose, mannose and galactose present in the treated solid component or hydrolysate to a fermentation product. A particular fermentation product is alcohol, such as ethanol. However, other compounds can be generated by adding the appropriate organism.

Many known microorganisms can be used in the present process to produce the desired chemicals. For instance, non-limiting examples of microorganisms are provided in Table 1 above. For particular embodiments that are directed to alcohol for use in biofuels, *Clostridia, Escherichia coli* (*E. coli*) and recombinant strains of *E. coli*, genetically modified strain of *Zymomonas mobilis* such as described in US2003/0162271, 60/847,813 and 60/847,856 (which disclosures are herein incorporated by reference) are some examples of such microorganism. The microorganisms may further be a yeast or a filamentous fungus of a genus *Saccharomyces, Kluyveromyces, Candida, Pichia, Schizosaccharomyces, Hansenula, Kloeckera, Schwanniomyces, Yarrowia, Aspergillus, Trichoderma, Humicola, Acremo-* nium, *Fusarium*, and *Penicillium*. Chemicals other than alcohol can also be produced by microorganisms such as *Bacillus, Lactobacillus, Streptococcus, Chlamydomonas, Rhizopus, Actinobacillus, Ralstonia, Rhodospirillum,* and *Eurotium*.

In certain embodiments, the lignocellulosic fermentation may also be performed with recombinant yeast engineered to ferment both hexose and pentose sugars to ethanol. Recombinant yeasts that can ferment one or both of the pentose sugars xylose and arabinose to ethanol are described in U.S. Pat. No. 5,789,210, U.S. Pat. No. 6,475,768, European Patent EP 1,727,890, European Patent EPI 863,901 and WO 2006/096130 which disclosures are herein incorporated by reference. Xylose utilization can be mediated by the xylose reductase/xylitol dehydrogenase pathway (for example, WO9742307 A1 19971113 and WO9513362 A1 19950518) or the xylose isomerase pathway (for example, WO2007028811 or WO2009109631). It is also contemplated that the fermentation organism may also produce fatty alcohols, for example, as described in WO 2008/119082 and PCT/US07/011923 which disclosure is herein incorporated by reference. In another embodiment, the fermentation may be performed by yeast capable of fermenting predominantly C6 sugars for example by using commercially available strains such as Thermosacc and Superstart.

Preferably, the lignocellulosic fermentation is performed at or near the temperature and pH optima of the fermentation microorganism. For example, the temperature may be from about 25° to about 55° C., or any amount there between. The dose of the fermentation microorganism will depend on other factors, such as the activity of the fermentation microorganism, the desired fermentation time, the volume of the reactor and other parameters. It will be appreciated that these parameters may be adjusted as desired by one of skill in the art to achieve optimal fermentation conditions.

The fermentation may be conducted in batch, continuous or fed-batch modes, with or without agitation. The fermentation system may employ a series of fermentation reactors. In some embodiment, the hydrolysis system and fermentation system may be conducted in the same vessel. In one embodiment, the hydrolysis can be partially completed and the partially hydrolyzed stream may be fermented. In one embodiment, a simultaneous saccharification and fermentation (SSF) process where hydrolysis system may be run until the final percent solids target is met and then the hydrolyzed biomass may be transferred to a fermentation system.

In certain embodiments, the fermentation system may produce a fermentation product comprising an alcohol stream that preferably contains at least one alcohol having 2 to 18 carbon atoms. In a particular embodiment, the fermentation product can be directed to the VOC solventless recovery system as described herein. In addition to or alternatively, it can recovery of the alcohol can be done separately.

To facilitate a better understanding of embodiments the present invention, the following examples of certain aspects of some embodiments are given. In no way should the following examples be read to limit, or define, the entire scope of the invention.

Illustrative Embodiments

Examples A and B used solid components obtained as described below.

Biomass Preparation

In this example, various samples of fresh chopped sorghum were mixed with a variety of added components as listed in Table 6 and were stored in a silage bag for about 20 days. The particular additives and respective addition rates are shown in Table 7.

TABLE 6

| 2011 Experiments | WITH ACID |
|---|---|
| Experiment # | 1 |
| Estimated mass | 450 kgs |
| Moisture Content | 76% |
| Storage Method | Silage bag |
| Yeast | Lallemand Liquid Yeast |
| Bacterial inhibitor | Lactrol |
| Enzyme | Novozymes Cellic CTec2 |
| Chop size | 3 mm |
| Result (gallons Ethanol/initial dry metric tonne) | 50 |
| Days in Storage | ~20 |

TABLE 7

| ADDITIVE | Rates |
|---|---|
| LACTROL | 3.2 g/wet ton |
| Lallemand Stabilized Liquid Yeast | 18 fl oz/wet ton |
| Novozymes Cellic CTec2 | 20 fl oz/wet ton |
| 9.3% Concentrated Sulfuric Acid | 3.8 L/wet ton |

VOC Recovery

The VOCs from the prepared biomass material of Examples A and B were recovered using a GEA SSD™ as the solventless recovery unit. Table 8 below provides certain properties of (i) the prepared biomass material fed into the solventless recovery unit, (ii) the solid component exiting the solventless recovery unit, and (iii) the operating conditions of the solventless recovery unit.

TABLE 8

| | Sample Feed composition |
|---|---|
| Liquid in Feed (%) | 80.2% |
| | Solid component |
| Liquid in Solid component (product) (%) | 60.21% |
| Solid component (product) Temperature (F) | 87 |
| | Operating Conditions |
| Heater Temperature (F) | 552 |
| Feed Rate (lb/min.) | 5.30 |
| Evaporation Rate (lb/min.) | 2.71 |
| Saturation Temperature (F) | 222 |
| Solid component production rate (lb/min.) | 2.55 |
| Vapor Temperature at Inlet (F) | 423 |
| Exhaust Temperature (F) | 235 |
| Operating Pressure (psig) | 3 |

Further Processing: Saccharification

Example A

The solid component obtained as described above was sent to National Renewable Energy Laboratory for testing along with other standard biomass samples. NREL performed reactivity screening on the following 5 samples:
1. Solid component sample (Sample #2)
2. Sugarcane bagasse standard (NIST 8491)
3. Monterey Pine standard (NIST 8493)
4. Wheat Straw standard (NIST 8494)
5. NREL corn stover standard (Kramer 33B51), which represents typical recalcitrance behavior of corn stover, e.g., "normal" to high expected recalcitrance behavior
6. NREL corn stover standard (Kramer 33A14), which has unusually low recalcitrance behavior Reactivity screening included sequential pretreatment and enzymatic hydrolysis assays. Pretreatment assays were performed using the Dionex ASE350 Solvent extractor by Ryan Ness. Pretreatment experiments were performed with dilute acid (1% v/v sulfuric acid: H2SO4) or hot water. For each catalyst, NREL performed experiments at 3 temperatures (140° C., 150° C., or 170° C. for acid catalysis, 170° C., 190° C., or 200° C. for hot water). The pretreatment assay includes a water rinse of the biomass samples, allowing for enzymatic hydrolysis without pretreated liquor interference. Enzymatic hydrolysis assays were performed in small shake flasks, according to a standard NREL protocol, which is substantially similar to the Laboratory Analytical Procedure "Enzymatic Saccharification of Lignocellulosic Biomass", found at http://www.nrel.gov/biomass/analytical_procedures.html.

NREL measured glucan and xylan release from pretreatment and enzymatic hydrolysis separately. The composition of the starting material was previously determined by NREL for those samples that did not have previous data available. Total glucan yield values were calculated using the following calculation:

$$Yield_{glucan} = \frac{glucan_{PT}(g) + \left(glucan_{EH}(g) \times \left(\frac{PT \text{ solids wet wt}(g)}{EH \text{ solids wet wt}(g)}\right)\right)}{glucan_{whole\ biomass}(g)}$$

Where: $glucan_{PT}(g)$ is the weight of glucan released into solution during the pretreatment $glucan_{EH}(g)$ is the weight of glucan released into solution during enzymatic hydrolysis PT solids wet wt (g) is the weight of the washed wet pretreated solids removed from the ASE 350

EH solids wet wt (g) is the weight of the washed wet pretreated solids used for enzymatic hydrolysis $glucan_{whole\ biomass}(g)$ is the weight of the glucan present in the starting biomass, based on the compositional analysis previously performed by NREL.

The yield calculation is the same for xylan, substituting xylan for glucan in the above equation. Further, it is noted that the results are derived using a small-scale enzymatic hydrolysis assay measures which may be different from results of larger-scale pretreatments.

The summary results for the 5 samples are shown in Table 9 below. Sample Kramer 33B51 was included as a control and an example of what can be expected for a corn stover sample under the specified conditions. This data set includes the specified NIST standards, the solid component sample, NREL's Kramer 33B51, and NREL's Kramer 33A14. NIST 8491 had enzyme failure for the hot water pretreatment at temperature 170, and the data is not available.

TABLE 9

April 2013

| Sample ID | Material type | Pretreatment catalyst | Oven Temp | Glucan yield | Xylan yield |
|---|---|---|---|---|---|
| Sample #2 | Sorghum | 1% v/v sulfuric acid | 140 | 73% | 71% |
|  |  |  | 150 | 95% | 82% |
|  |  |  | 170 | 103% | 68% |
| NIST 8491 | Bagasse |  | 140 | 61% | 79% |
|  |  |  | 150 | 77% | 84% |
|  |  |  | 170 | 88% | 49% |
| NIST 8493 | Pine |  | 140 | 22% | 57% |
|  |  |  | 150 | 26% | 69% |
|  |  |  | 170 | 39% | 62% |
| NIST 8494 | Wheat Straw |  | 140 | 83% | 78% |
|  |  |  | 150 | 99% | 84% |
|  |  |  | 170 | 105% | 67% |
| Kramer 33B51 | Corn Stover |  | 140 | 88% | 81% |
|  |  |  | 140 | 90% | 81% |
|  |  |  | 140 | 91% | 81% |
|  |  |  | 150 | 104% | 86% |
|  |  |  | 170 | 108% | 62% |
| Kramer 33A14 | Corn Stover |  | 130 | 91% | 78% |
| Sample #2 | Sorghum | Hot Water | 170 | 55% | 40% |
|  |  |  | 190 | 84% | 68% |
|  |  |  | 200 | 93% | 66% |
| NIST 8491 | Bagasse |  | 170 | N/A | N/A |
|  |  |  | 190 | 73% | 76% |
|  |  |  | 200 | 90% | 75% |
| NIST 8493 | Pine |  | 170 | 27% | 47% |
|  |  |  | 190 | 42% | 68% |
|  |  |  | 200 | 37% | 66% |
| N IST 8494 | Wheat Straw |  | 170 | 56% | 43% |
|  |  |  | 190 | 83% | 69% |
|  |  |  | 200 | 96% | 76% |
| Kramer 33B51 | Corn Stover |  | 170 | 64% | 42% |
|  |  |  | 170 | 65% | 45% |
|  |  |  | 170 | 68% | 48% |
|  |  |  | 190 | 87% | 71% |
|  |  |  | 200 | 99% | 75% |
| Kramer 33A14 | Corn Stover |  | 200 | 103% | 77% |

Figure 6:
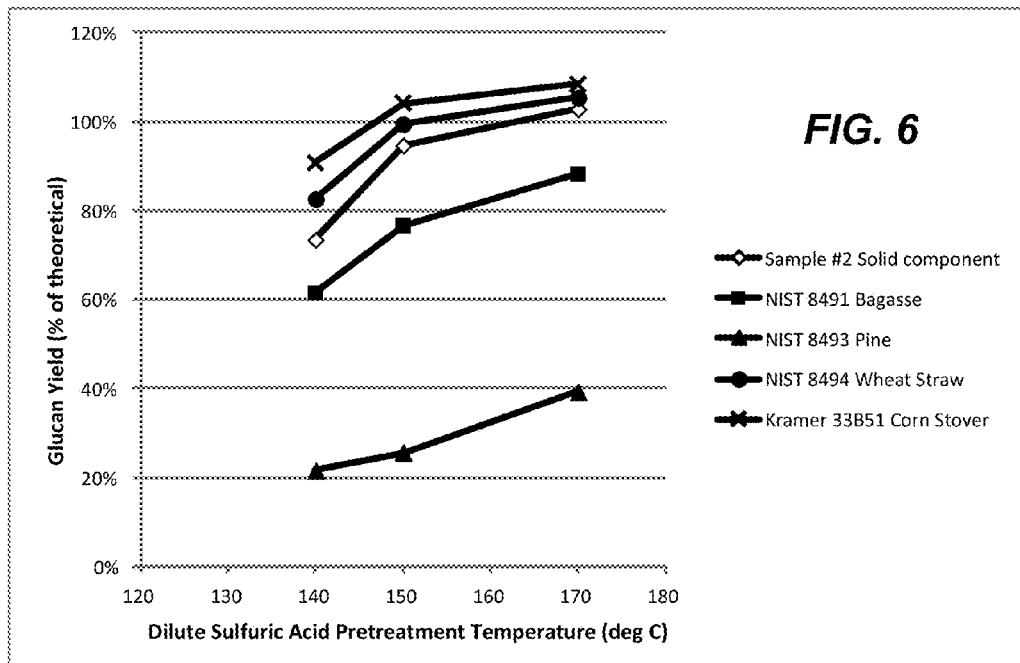
FIG. 6 shows a graph of pretreatment temperature vs. % of glucan yield for a dilute sulfuric acid pretreatment according to certain aspects of the invention.
Figure 7:
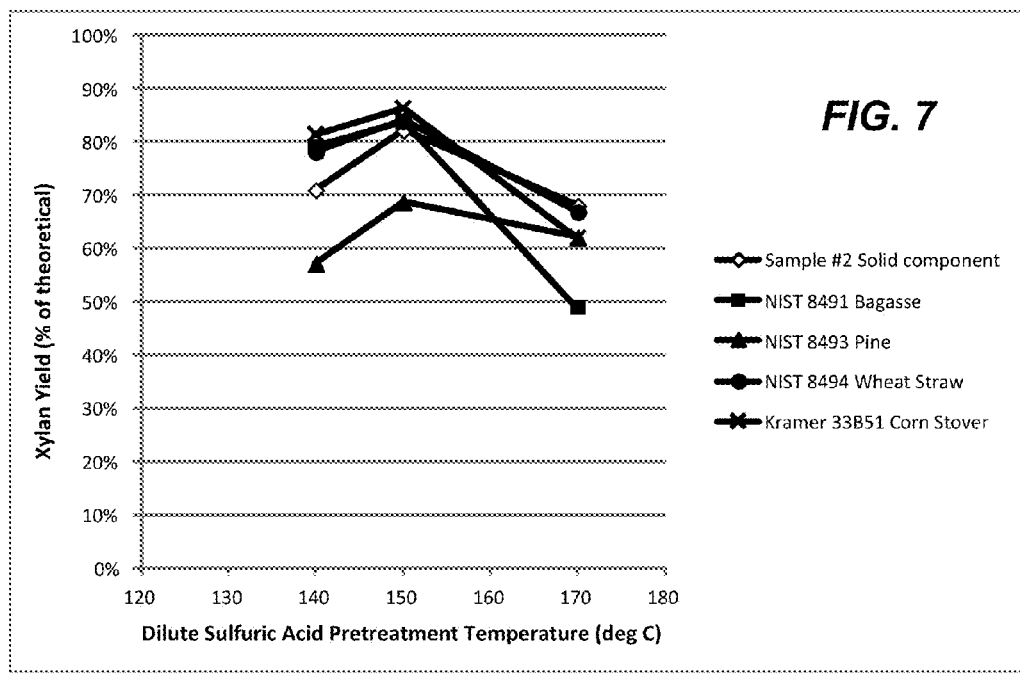
FIG. 7 shows a graph of pretreatment temperature vs. % of xylan yield for a dilute sulfuric acid pretreatment according to certain aspects of the invention.
Figure 8:
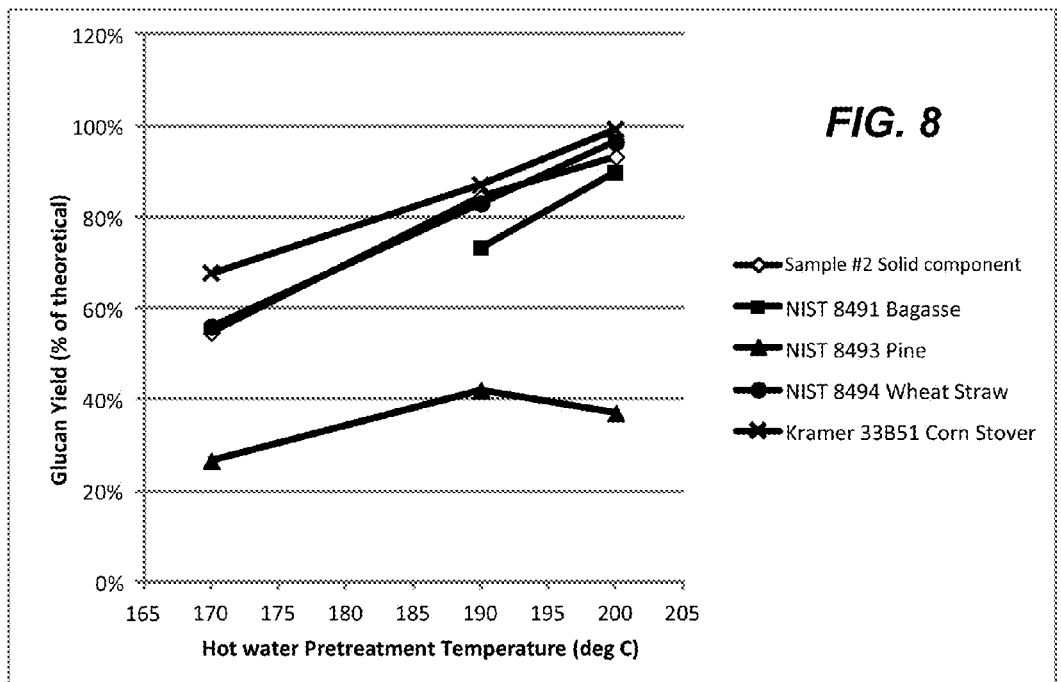
FIG. 8 shows a graph of pretreatment temperature vs. % of glucan yield for a hot water pretreatment according to certain aspects of the invention.
Figure 9:
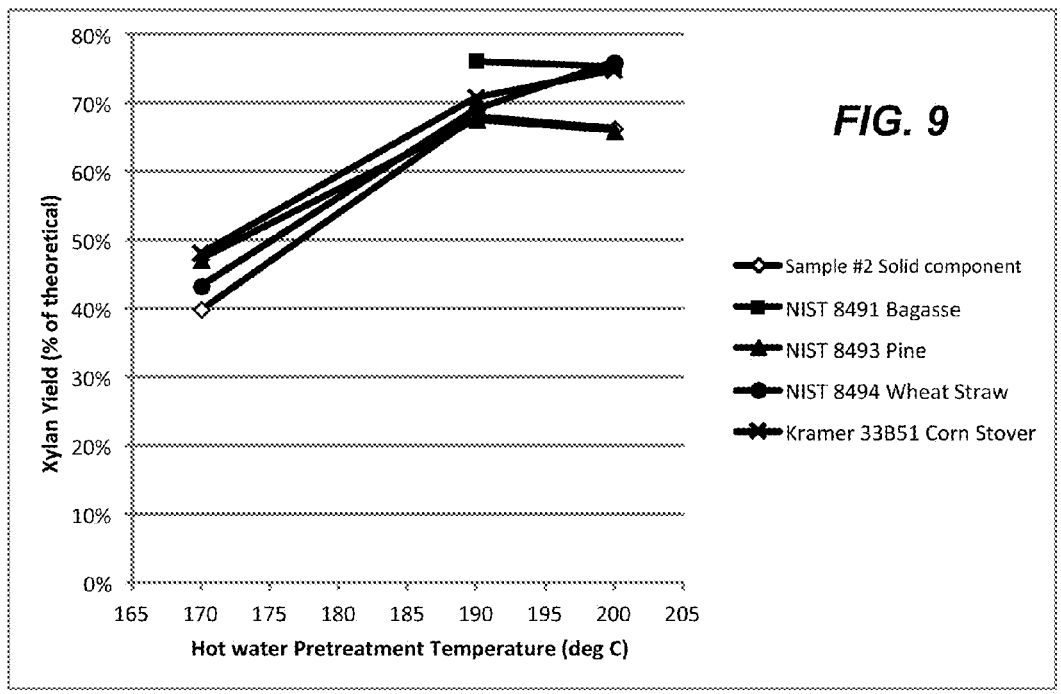
FIG. 9 shows a graph of pretreatment temperature vs. % of xylan yield for a hot water treatment according to certain aspects of the invention.

FIG. 6 shows a graph of pretreatment temperature vs. % of glucan yield and FIG. 7 shows a graph of pretreatment temperature vs. % of xylan yield for the dilute sulfuric acid treatment. FIG. 8 shows a graph of pretreatment temperature vs. % of glucan yield and FIG. 9 shows a graph of pretreatment temperature vs. % of xylan yield for the hot water treatment.

Both sets of graphs show that the solid component sample (Sample #2) required about the same processing energy, in terms of pretreatment temperature changes, for achieving high glucan and xylan yields as wheat straw and corn stover. The solid component sample (Sample #2) required markedly less energy to yield glucose from cellulose compared to sugar cane bagasse and pine wood. This means that the solid component of embodiments of the invention can be introduced into existing dilute acid or hot water pretreatment equipment with minimal equipment and operational changes as compared to sugar cane bagasse and pine wood. Further, the graphs show the solid component sample requires less severe pretreatment conditions to achieve similar or comparable xylose production than sugar cane bagasse and pine wood. Lower severity pretreatment conditions include using solutions with the same pH and same temperature with lower treatment time, which increases efficiency by allowing for more material to be treated during the same time period.

In all cases xylan yield peaked at 150 degrees C. then decreased at 170 degrees C. This is commonly found, and is most likely due to over-processing of the five-carbon sugar xylose at the higher temperatures, where the xylose degrades into furfural reaction products.

Example B

Alpha-Hydroxyethane Sulfonic Acid

This is the general procedure for samples B.1 through B.3 of Example B. The conditions utilized and the results are in Table 10. In particular, column B lists the target temperature, column C lists the time at reaction temperature, column D lists the amount of solid component placed in the reactor ("charged solid component"), column E lists the approximate wt % alpha-hydroxyethane sulfonic acid (HESA) solution based on the amount of total reaction mixture, column F lists the estimated Bone Dry Biomass (BDBM), column G lists the % of the original BDBM material dissolved or removed, column H lists the % glucose recovered in the filtrate, and column I lists the % xylose recovered in the filtrate.

A certain amount of the solid component obtained as described above was placed into a 2 litters autoclave equipped with a DiComp IR probe. A certain amount of α-hydroxyethane sulfonic acid (HESA) solution was added to the solid component by gentle pouring over the solid component in the reactor.

The reaction mixture was heated to the target temperature and held for the stated period of time. The reaction mixture was not stirred. The heating was discontinued. The reactor was purged with a slow nitrogen stream for a few minutes to eliminate any sulfur dioxide in the gas cap. The reactor was cooled to room temperature and purged once more with nitrogen.

The reactor content was transferred to a Buchner funnel and vacuum filtered over Whatman 541 hardened ashless 185 mm filter paper. As much liquid as possible was removed from the reactor content. The cumulative weight of the filtrate and liquids removed was obtained. The filtrate was then analyzed by HPLC and the recovery of materials from the biomass calculated by comparison to the amount of the precursors in present in the biomass.

Examples B.1-B.3 show that the solid components obtained according to certain aspects of the present invention perform better than corn stover. In particular, the treatment with HESA dissolved more than 50% by weight of the starting solid component on a dry biomass to dry biomass basis. In contrast, runs under analogous conditions for corn stover resulted in a dissolution or removal of approximately one third of the biomass.

In addition, about 90% of xylose was recovered as monomeric xylose based on the estimated starting xylan. Analysis of the residual pretreated solid component showed virtually all of the hemicelluloses had been removed from the biomass. Further, about 10% of the glucan in the starting solid component biomass was converted into glucose. In comparison to corn stover, only about 75 to 80% of the xylan was recovered as monomeric xylose. The xylan in the residual pretreated material remains at approximately 15% in the case of corn stover. This indicates that the solid component obtained according to aspects of the invention is a less recalcitrant biomass than other biomass sources (such as wheat straw, corn stover, or bagasse). Further, these results were achieved without any stirring or agitation of the reaction content.

Samples B.1 to B.3 were washed with distilled water through a Buchner funnel and further subject to enzymatic hydrolysis. An unwashed sample and a sample that was not treated ("native") were also subject to the same enzymatic hydrolysis conditions for comparison purposes. There were two enzyme dosing conditions: (1) a low enzyme dosing comprising using 0.0041 grams of CTEC2 cellulase enzyme per gram of hydrolysate solution, and (2) a high enzyme dosing comprising using 0.0122 grams of CTEC2 cellulase enzyme solution per gram of hydrolysate solution. The concentration of the hydrolysate solution, washed and unwashed, is 10% w/w of undissolved solids. Table 11 shows the glucose concentration generated for each sample hydrolyzed under different hydrolysis conditions over a time period of about 144 hours.

TABLE 11

| Wash condition | Hydrolysis condition | Sample | 0 hour | 24 hours | 48 hours | 72 hours | 144 hours |
|---|---|---|---|---|---|---|---|
| Washed with water | Low enzyme | B.1 | 2.5 | 38.5 | 46.4 | 50.5 | 54.6 |
| | | B.2 | 3.8 | 39.7 | 46.7 | 51.9 | 54.7 |
| | | B.3 | 3.9 | 33.8 | 40.6 | 42.2 | 47.9 |
| | | Native | 0.4 | 5.6 | 4.0 | 0.6 | 0.8 |
| | High enzyme | B.1 | 3.0 | 64.6 | 78.7 | 69.7 | 54.6 |
| | | B.2 | 4.1 | 55.8 | 57.1 | 59.7 | 63.5 |
| | | B.3 | 3.4 | 49.5 | 53.1 | 57.6 | 60.0 |
| | | Native | 0.4 | 8.9 | 8.5 | 3.3 | 4.4 |

Glucose concentration (g/L) at different hydrolysis time (hours)

TABLE 10

| A Sample | B Reaction Temp. (° C.) | C Time at Temp. (hr) | D Amount of Solid Component charged (g) | E Acid Concentration (% Wt reactor content) | F BDBM charged (g) | G Dissolved BDBM (% original) | H % Glucose Recovery in Filtrate* | I % Xylose Recovery in Filtrate** |
|---|---|---|---|---|---|---|---|---|
| B.1 | 120 | 1 | 299.9 | 3.83 | 124.61 | 55.7 | 11.7 | 89.5 |
| B.2 | 120 | 1 | 300.57 | 5 | 130.54 | 52.26 | 11.7 | 88.8 |
| B.3 | 100 | 1 | 263.34 | 11.0 | 120.48 | 51.19 | 8.9 | 80.9 |

TABLE 11-continued

| Wash condition | Hydrolysis condition | Sample | 0 hour | 24 hours | 48 hours | 72 hours | 144 hours |
|---|---|---|---|---|---|---|---|
| Unwashed | Low enzyme | B.1 | 4.8 | 28.2 | 33.8 | 36.4 | 38.5 |
| | | B.2 | 4.6 | 25.5 | 29.9 | 33.1 | 38.2 |
| | | B.3 | 5.2 | 26.8 | 31.3 | 33.9 | 39.6 |

Glucose concentration (g/L) at different hydrolysis time (hours)

TABLE 11-continued

| Wash condition | Hydrolysis condition | Sample | Glucose concentration (g/L) at different hydrolysis time (hours) | | | | |
|---|---|---|---|---|---|---|---|
| | | | 0 hour | 24 hours | 48 hours | 72 hours | 144 hours |
| | | Native | 1.6 | 8.4 | 5.6 | 6.0 | 5.8 |
| | High enzyme | B.1 | 4.5 | 40.1 | 45.0 | 46.9 | 48.4 |
| | | B.2 | 4.4 | 38.5 | 45.6 | 46.5 | 50.3 |
| | | B.3 | 4.8 | 33.8 | 38.1 | 40.4 | 45.5 |
| | | Native | 1.5 | 8.5 | 8.9 | 7.6 | 8.1 |

Figure 10:
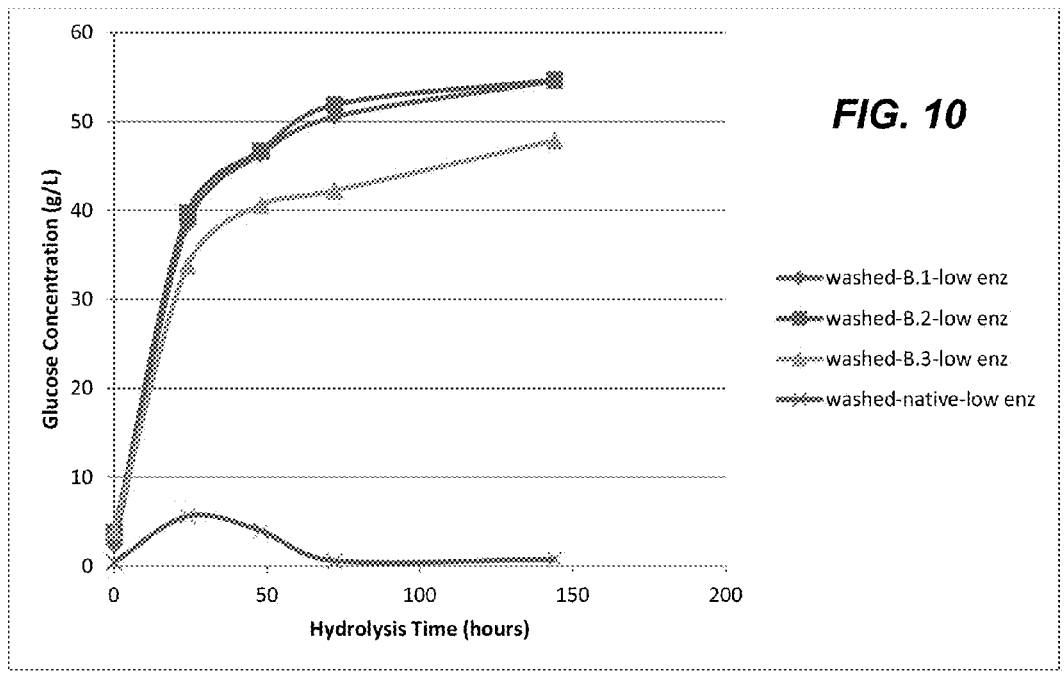
FIG. 10 is a graph of the glucose concentration over time of washed samples of an embodiment of pretreated solid components treated with low enzyme level according to certain aspects of the invention.
Figure 11:
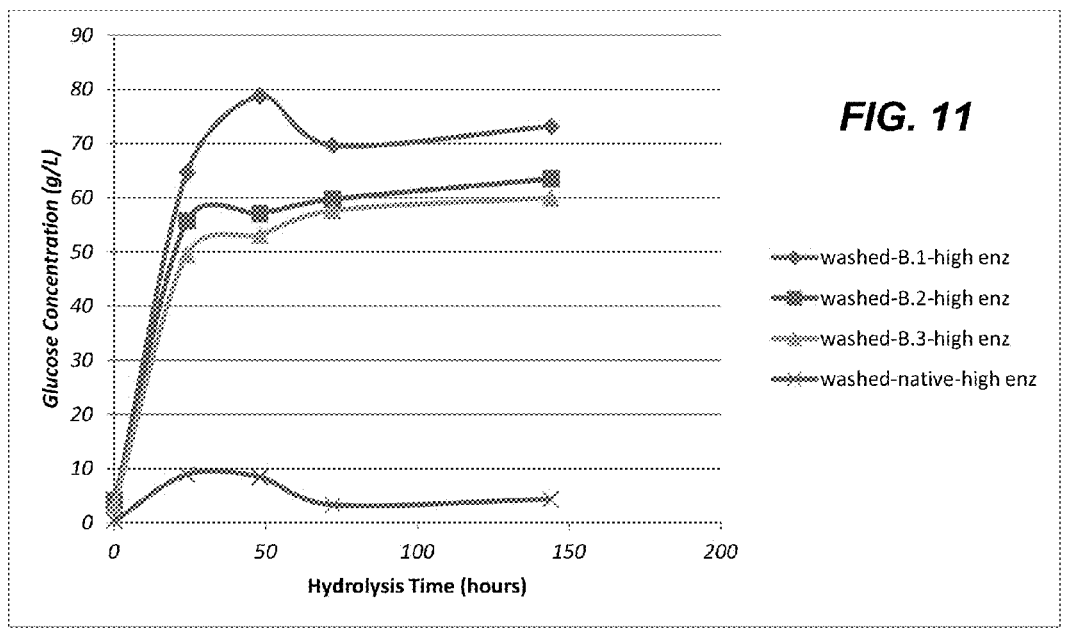
FIG. 11 is a graph of the glucose concentration over time of washed samples of an embodiment of pretreated solid components treated with high enzyme level according to certain aspects of the invention.
Figure 12:
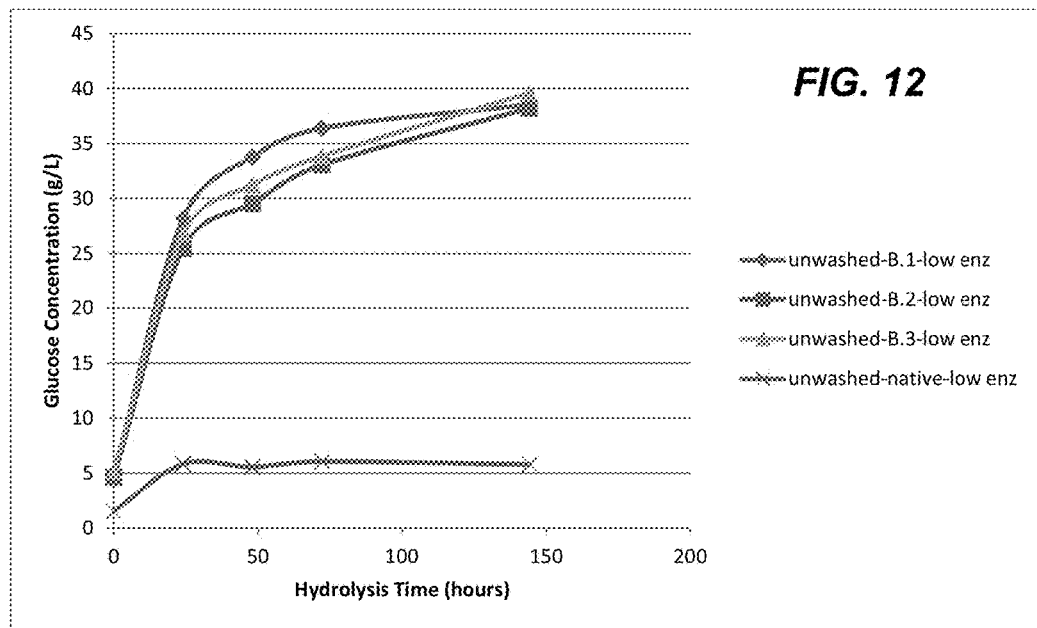
FIG. 12 is a graph of the glucose concentration over time of unwashed samples of an embodiment of pretreated solid components treated with low enzyme level according to certain aspects of the invention.
Figure 13:
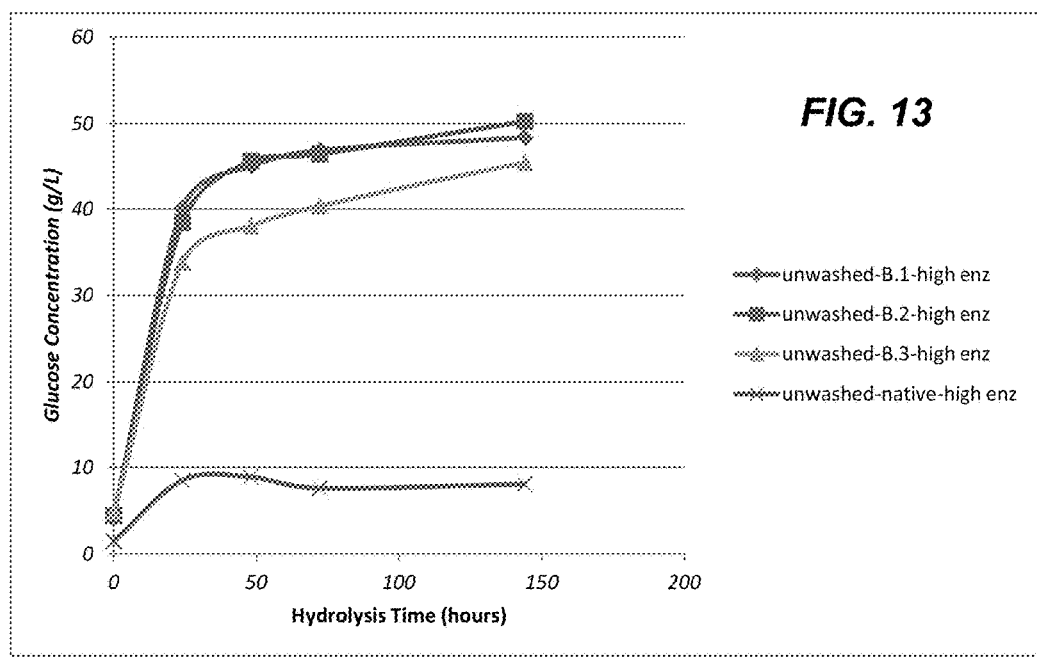
FIG. 13 is a graph of the glucose concentration over time of unwashed samples of an embodiment of pretreated solid components treated with low enzyme level according to certain aspects of the invention.

FIG. 10 is a graph of the glucose concentration of washed samples treated with low enzyme level over the hydrolysis treatment time period at the following time points: 0 hour, 24 hours, 48 hours, 72 hours, and 144 hours. FIG. 11 is a graph of the glucose concentration of washed samples treated with high enzyme level over the hydrolysis treatment time period at the following time points: 0 hour, 24 hours, 48 hours, 72 hours, and 144 hours. FIG. 12 is a graph of the glucose concentration of unwashed samples treated with low enzyme level over the hydrolysis treatment time period at the following time points: 0 hour, 24 hours, 48 hours, 72 hours, and 144 hours. FIG. 13 is a graph of the glucose concentration of unwashed samples treated with high enzyme level over the hydrolysis treatment time period at the following time points: 0 hour, 24 hours, 48 hours, 72 hours, and 144 hours.

These samples show that the pretreated solid component according to certain embodiments of the invention could be hydrolyzed to glucose in about 48 hours. This demonstrates that the pretreated material is does not prohibit enzyme activity.

Example C

In the following examples, a solid component biomass material obtained according to certain aspects of the invention was treated with alpha-hydroxyethane sulfonic acid and subsequently subject to enzymatic hydrolysis.

Biomass Preparation

For Example C, various samples of fresh chopped sorghum were mixed with a variety of added components as listed in Table 12 and were stored in a silage bag for about 20 days. The particular additives and respective addition rates are shown in Table 13.

TABLE 12

| 2011 Experiments | WITH ACID |
|---|---|
| Experiment # | 1 |
| Estimated mass | 450 kgs |
| Moisture Content | 76% |
| Storage Method | Silage bag |
| Yeast | Lallemand Liquid Yeast |
| Bacterial inhibitor | Lactrol |
| Enzyme | Novozymes Cellic CTec2 |
| Chop size | 3 mm |
| Result (gallons Ethanol/initial dry metric tonne) | 50 |
| Days in Storage | ~20 |

TABLE 13

| ADDITIVE | Rates |
|---|---|
| LACTROL | 3.2 g/wet ton |
| Lallemand Stabilized Liquid Yeast | 18 fl oz/wet ton |
| Novozymes Cellic CTec2 | 20 fl oz/wet ton |
| 9.3% Concentrated Sulfuric Acid | 3.8 L/wet ton |

VOC Recovery

The VOCs from the prepared biomass material of Example C were recovered using a GEA SSD™ as the solventless recovery unit. Table 14 below provides certain properties of (i) the prepared biomass material fed into the solventless recovery unit, (ii) the solid component exiting the solventless recovery unit, and (iii) the operating conditions of the solventless recovery unit.

TABLE 14

| | Sample |
|---|---|
| | Feed composition |
| Liquid in Feed (%) | 80.2% |
| | Solid component |
| Liquid in Solid component (product) (%) | 31.4% |
| Solid component (product) Temperature (F) | 90 |
| | Operating Conditions |
| Heater Temperature (F) | 516 |
| Feed Rate (lb/min.) | 5.30 |
| Evaporation Rate (lb/min.) | 3.93 |
| Saturation Temperature (F) | 287 |
| Solid component production rate (lb/min.) | 1.03 |
| Vapor Temperature at Inlet (F) | 428 |
| Exhaust Temperature (F) | 370 |
| Operating Pressure (psig) | 40 |

Further Processing: Saccharification

Into a 4 liter bottle was added 2160.02 grams of deionized water and 540.12 grams of 40% wt. HESA were mixed to form 8.5% wt. HESA solution. Into a one gallon Parr Instruments C276 autoclave equipped with a DiComp IR probe was placed 433.82 grams of the solid component of Example C. The solid component was estimated to have 289.67 grams of BDBM. The acid solution was gently poured over the wet biomass in the reactor. The reactor contained a mixture comprising approximately 9.53% wt. dry biomass in contact with a 7.3% wt. HESA solution (based on the total reactor content).

The reaction mixture was heated to 120 degrees C. and held for the stated period of time. The reactor content was stirred initially at 100 rpm, but as the reaction heats to 120° C. the contents thin and the stir rate is increased to 250 then 400 rpm. The reactor was held at 120° C. for 1 hour. The heating was discontinued. The reactor was purged with a slow nitrogen stream for a few minutes to eliminate any sulfur dioxide in the gas cap. The reactor was cooled to room temperature and purged once more with nitrogen.

The reactor content was transferred to a Buchner funnel and vacuum filtered over Whatman 541 hardened ashless 185 mm filter paper. As much liquid as possible was removed from the reactor content. The cumulative weight of the filtrate and liquids removed was obtained. The filtrate was then analyzed by HPLC and the recovery of materials from the biomass calculated by comparison to the amount of the precursors in present in the biomass. The % of glucose recovered was 11.3%, based on the theoretical amount of glucose available in the biomass. The % of xylose recovered was 91%, based on the theoretical amount of xylose available in the biomass.

The treated sample was further subject to enzymatic hydrolysis. 144 grams of the material from HESA treatment were washed 3 times with 500 mL deionized water. After the first wash, the pH of the material was adjusted to 10. The liquid was then drained, and water was added, and the pH was adjusted to 5.6. In 1 L of water with about 144 grams of washed material, 50 grams of CTEC2 cellulase were added. The solution was shaken at 53 degrees Celsius for 3 days at which time the contents were measured to be: Cellobiose: 1.93 g/L, Glucose: 52.6 g/L, Xylose: 6.12 g/L, Arabinose: 0 g/L, Glycerol: 1.4 g/L, Acetic Acid: 0.92 g/L, Ethanol: 0.0 g/L.

Fermentation

The hydrolysis mixture was then fermented directly using *Bacillus subtilis* and *Saccharomyces cerevisiae* without further separation. The conditions and results are as follows.

Media and Microbes:

A preparation (Stock) of 3 g/L of peptone Type I from meat Sigma-Aldrich P7750 and 5 g/L of yeast extract Sigma-Aldrich 92144 was prepared for combination with the hydrolysis mixture. Then 30 mL of the peptone/yeast extract Stock was added with 20 mL of hydrolysis mixture, and 1 mL of inoculum for each microbe. Microbes used were *Saccharomyces cerevisiae* (ATCC 24702) and *Bacillus subtilis* (ATCC 31785) which were reconstituted in tryptic soy broth, grown for 48 hours, then used directly as 1 mL inocula into 250 mL Erlenmeyer flasks. Flasks were shaken for 2 days at 33 degrees C. then harvested for analysis.

Chemical Analyses:

Sucrose, succinic acid, lactic acid, propionic acid, 2,3-butanediol, and 1,2-butanediol were analyzed by: Instrument: Shimadzu HPLC system, Controller: SCL-10A, Pump: LC-20AD, Autosampler: SIL-10A, Oven: CTO-10A, Detector: RID-10A, Column. Bio-Rad Aminex HPX-87H (300×7.8 mm), Mobile Phase: 5 mM Sulfuric Acid in Water, Flow Rate: 0.6 ml/min, Temperature: 30° C., Run Time: 65 min.

Cellobiose, glucose, xylose, arabinose, glycerol, acetic acid, and ethanol were analyzed using an HPLC Dionex ultimate 3000 Setup with samples run at 65 C, a flow rate of 6 mL/min with 25 minute run times, a RI-101 Shodex column held at 50 C. Computer Program used to analyze is chromeleon console.

Results:

Microbial Growth:

Microbial growth using the hydrolysis mixture was confirmed by the decreasing amount of glucose from time zero flasks to the day 2 harvested flasks. For example, *Bacillus subtilis* culture began with 20.5 g/L glucose, which at day 2 was measured to be 0.25 g/L. Likewise, *Saccharomyces cerevisiae* culture began with 19.7 g/L glucose and at day 2 this had reduced to 0.23 g/L glucose. Both flasks also exhibited characteristic smells as well as an increase in observable turbidity. For example, the *S. cerevisiae* smelled strongly of bread. In contrast, cultures which were set up identically but received minimal salts media in place of the hydrolysis mixture showed no signs of microbial growth.

Microbial Conversion to Products:

Tables 16 and 17 below show the chemicals analyzed from the fermentation product of *Bacillus subtilis* and *Saccharomyces cerevisiae*, respectively. A "0" indicates that the chemical was not detected by the instrument. The notation "nd" indicates that the sample was not submitted for measurement for those chemicals.

TABLE 16

Bacillus subtilis

| | time 0 | | Day 2 | |
|---|---|---|---|---|
| | without hydrolysis mixture | with hydrolysis mixture | without hydrolysis mixture | with hydrolysis mixture |
| Compound | g/L | g/L | g/L | g/L |
| Cellobiose | 0 | 0.71 | 0 | 0.23 |
| Glucose | 0 | 20.5 | 0 | 0.26 |
| Xylose | 0 | 2.5 | 0 | 1.16 |
| Arabinose | 0 | 0 | 0 | 0 |
| Glycerol | 0 | 0.093 | 0 | 0 |
| acetic acid | 0 | 0.13 | 0 | 0 |
| Ethanol | 0 | 0 | 0 | 0 |
| Sucrose | nd | nd | 0 | 0.18 |
| succinic acid | nd | nd | 0 | 1.1 |
| lactic acid | nd | nd | 0 | 0 |
| propionic acid | nd | nd | 0 | 10.1 |
| 2,3-butanediol | nd | nd | 0 | 0.21 |
| 1,2-butanediol | nd | nd | 0 | 0.24 |

TABLE 17

Saccharomyces cerevisiae

| | time 0 | | Day 2 | |
|---|---|---|---|---|
| | without hydrolysis mixture | with hydrolysis mixture | without hydrolysis mixture | with hydrolysis mixture |
| Compound | g/L | g/L | g/L | g/L |
| Cellobiose | 0 | 0.684 | 0 | 0.379 |
| Glucose | 0 | 19.7 | 0 | 0.23 |
| Xylose | 0 | 2.51 | 0 | 0.97 |
| Arabinose | 0 | 0 | 0 | 0 |
| Glycerol | 0 | 0.086 | 0.016 | 0.64 |
| acetic acid | 0 | 0.07 | 0.026 | 0.16 |
| Ethanol | 0 | 0.118 | 0.118 | 10.9 |
| Sucrose | nd | nd | 0 | 0 |
| succinic acid | nd | nd | 0 | 0.07 |
| lactic acid | nd | nd | 0 | 0.3 |
| propionic acid | nd | nd | 0 | 0 |
| 2,3-butanediol | nd | nd | 0 | 0 |
| 1,2-butanediol | nd | nd | 0 | 0 |

Based on HPLC of the samples, other compounds were also generated. For example, in the *B. subtilis* sample, 2-pentanone and 3-hydroxy, 2-butanone were also identified. In the *S. cerevisiae* sample, Acetaldehyde, n-propanol, and 2,3-methyl, 1-propanol were also identified.

This Example shows that the microorganisms used the glucose in the hydrolysis mixture to produce particular chemical compounds. For example, *B. subtilis* produced 10.1 g/L propionic acid, 1.1 g/L succinic acid, 0.21 g/L 2,3-butanediol and 0.24 g/L butanediol. *S. cerevisiae* produced 0.64 g/L glycerol, 0.16 g/L acetic acid, and 10.9 g/L ethanol. This shows that the glucose in the hydrolysis mixture was available to the microorganisms and further that the hydrolysis mixture was not toxic to the microorganisms.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

We claim:

1. A method for processing a prepared biomass material comprising:
   (i) introducing a prepared biomass material to a pressurized compartment of a recovery system, wherein the prepared biomass material contains an initial liquid content comprising ethanol and wherein the prepared biomass material is generated by adding to a lignocellulosic biomass at least one additive selected from the group consisting of a microbe, an acid, an enzyme, or any combination thereof and storing the lignocellulosic biomass material with at least one additive for at least 24 hours;
   (ii) contacting the prepared biomass material with a superheated vapor stream in the pressurized compartment to vaporize at least a portion of the initial liquid content in the prepared biomass material to provide a vapor component, wherein the superheated vapor stream is about 100° C. to about 375° C., and the recovery system is operated at a pressure range of about 3 psig to about 60 psig;
   (iii) retaining an amount of the vapor component comprising ethanol in a range of 1 wt % to 50 wt % for use as part of the superheated vapor stream;
   (iv) releasing from the recovery system at least a portion of the prepared biomass material after vaporization to provide a solid component; and
   (vi) contacting at least a portion of the solid component with a solution adapted to facilitate saccharification.

2. The method of claim 1 wherein the solution adapted to facilitate saccharification comprises water having a temperature of at least about 170 degrees C.

3. The method of claim 1 wherein the solution adapted to facilitate saccharification comprises an acid solution adapted to hydrolyze at least a portion of the solid component to produce a product comprising a fermentable sugar.

4. The method of claim 3 wherein the acid solution comprises at least one alpha-hydroxysulfonic acid.

5. The method of claim 4 wherein the alpha-hydroxysulfonic acid is present in an amount of from about 1% wt. to about 55% wt., based on the solution.

6. The method of claim 4 wherein the alpha-hydroxysulfonic acid is produced from (a) a carbonyl compound or a precursor to a carbonyl compound with (b) sulfur dioxide or a precursor to sulfur dioxide and (c) water.

7. The method of claim 4 wherein the solid component is contacted with the acid solution at a temperature in a range of about 50 degrees C. to about 150 degrees C. and a pressure within the range of 1 barg to about 10 barg.

8. The method of claim 4 wherein further comprising removing the alpha-hydroxysulfonic acid in its component form from the product by heating and/or reducing pressure to produce an acid-removed product containing at least one fermentable sugar substantially free of the alpha-hydroxysulfonic acid.

9. The method of claim 8 further comprising hydrolyzing and fermenting the acid-removed product to generate a fermented product comprising a plurality of VOCs.

10. The method of claim 1 wherein the lignocellulosic biomass is selected from the group consisting of sorghum, sugar cane, corn, tropical corn, sugar beet, energy cane, and any combination thereof.

11. The method of claim 1 wherein the pressurized compartment comprises a cylindrical body in a shape of a loop within which the superheated vapor stream flows.

12. The method of claim 1 wherein the separating step is achieved using a cyclone separating component coupled to the pressurized compartment, wherein the cyclone separating component is configured to discharge the separated solid component from the pressurized component.

13. The method of claim 1 wherein the biomass has an average size distribution of about 3 mm to about 80 mm.

14. The method of claim 1 further comprises feeding at least a portion of the solid component from the recovery system directly to the contacting step.

15. The method of claim 1 wherein the solid component contacted with the solution adapted to facilitate saccharification is not agitated during at least a portion of the contact.

16. A method for processing a prepared biomass material comprising:
   contacting a solid component of a prepared biomass material with a solution adapted to facilitate saccharification, wherein the solid component is generated by a method comprising:
   introducing the prepared biomass material to a pressurized compartment of a recovery system, wherein the prepared biomass material is generated by adding to a lignocellulosic biomass at least one of a microbe, an acid, and an enzyme; and storing the lignocellulosic biomass for at least about 24 hours;
   contacting the prepared biomass material with a superheated vapor stream in the pressurized compartment to vaporize at least a portion of an initial liquid content in the prepared biomass material to provide a vapor component, wherein the initial liquid content comprises ethanol, and wherein the superheated vapor stream is about 100° C. to about 375° C. and the recovery system is operated at a pressure range of about 3 psig to about 60 psig;
   retaining in the recovery system an amount of the vapor component comprising ethanol in a range of 1 wt % to 50 wt % for use as part of the superheated vapor stream;
   releasing from the recovery system at least a portion of the prepared biomass material after vaporization to provide the solid component for said contact with the solution adapted to facilitate saccharification.

17. The method of claim 1 wherein the initial liquid content in the biomass material is up to about 80 wt % based on the biomass material.

18. The method of claim 1 wherein the initial liquid content comprises from about 2 wt % to about 50 wt % ethanol based on the initial liquid content.

19. The method of claim 1 wherein at least a portion of the solid component exiting the recovery system has a temperature of less than about 50 degrees C.

20. The method of claim 16 wherein the lignocellulosic biomass comprises a crop selected from the group consisting of sorghum, sugar cane, corn, tropical corn, sugar beet, energy cane, and any combination thereof.

21. The method of claim 1 further comprising: removing less than 100% of the ethanol in the prepared biomass material.

22. The method of claim 1 comprising: removing in a range of 50% to 90% of the ethanol in the prepared biomass material.

23. The method of claim 1 wherein the superheated vapor stream comprises between about 1 wt % and about 50 wt % ethanol.

24. The method of claim 1 wherein the superheated vapor stream comprises between 4 wt % and about 15 wt % ethanol.

25. The method of claim 16 wherein the solution adapted to facilitate saccharification comprises an acid solution adapted to hydrolyze at least a portion of the solid component to produce a product comprising a fermentable sugar, wherein the acid solution comprises at least one alpha-hydroxysulfonic acid.

26. The method of claim 1, wherein during steady state operation of the recovery system, the superheated vapor stream consists essentially of the vapor component.

27. The method of claim 16 wherein at least a portion of the solid component exiting the recovery system has a temperature of less than about 50 degrees C.

28. The method of claim 16 wherein the superheated vapor stream comprises between 4 wt % and about 15 wt % ethanol.

29. The method of claim 16, wherein during steady state operation of the recovery system, the superheated vapor stream consists essentially of the vapor component.

* * * * *